(12) United States Patent
Yan et al.

(10) Patent No.: US 11,697,845 B2
(45) Date of Patent: Jul. 11, 2023

(54) DIRECTING TREATMENTS FOR GLIOBLASTOMA BASED ON IDENTIFYING A SOMATIC STRUCTURAL REARRANGEMENT UPSTREAM FROM TERT GENE

(71) Applicant: Duke University, Durham, NC (US)

(72) Inventors: Hai Yan, Durham, NC (US); Bill H. Diplas, Durham, NC (US)

(73) Assignee: Duke University, Durham, NC (US)

( * ) Notice: Subject to any disclaimer, the term of this patent is extended or adjusted under 35 U.S.C. 154(b) by 273 days.

(21) Appl. No.: 16/979,422

(22) PCT Filed: Mar. 8, 2019

(86) PCT No.: PCT/US2019/021356
§ 371 (c)(1),
(2) Date: Sep. 9, 2020

(87) PCT Pub. No.: WO2019/173717
PCT Pub. Date: Sep. 12, 2019

(65) Prior Publication Data
US 2021/0002702 A1  Jan. 7, 2021

Related U.S. Application Data

(60) Provisional application No. 62/640,900, filed on Mar. 9, 2018.

(51) Int. Cl.
| | | |
|---|---|---|
| *C12Q 1/68* | (2018.01) | |
| *C12Q 1/686* | (2018.01) | |
| *C12Q 1/6841* | (2018.01) | |
| *C12Q 1/6881* | (2018.01) | |
| *C12Q 1/6886* | (2018.01) | |

(52) U.S. Cl.
CPC ........... *C12Q 1/686* (2013.01); *C12Q 1/6841* (2013.01); *C12Q 1/6881* (2013.01); *C12Q 1/6886* (2013.01)

(58) Field of Classification Search
CPC .................................................. C12Q 1/6886
See application file for complete search history.

(56) References Cited

U.S. PATENT DOCUMENTS

2011/0065113 A1 * 3/2011 Chinnaiyan ............. A61P 13/08
435/6.12

FOREIGN PATENT DOCUMENTS

WO  2015116530 A1  8/2015

OTHER PUBLICATIONS

Barthel et al., Nature Genetics 49(3), 349-357 (2017). (Year: 2017).*
Jafri et al., Genome Medicine 8(69), 1-18 (2016). (Year: 2016).*
Jun. 26, 2019—(WO) International Search Report—PCT/US2019/021356.
Diplas et al. "The genomic landscape of TERT promoter wildtype-IDH wildtype glioblastoma" Nature Communications, 2018, vol. 9, pp. 1-11.
Valentijn et al. "TERT rearrangements are frequent in neuroblastoma and identify aggressive tumors" Nature Genetics, Dec. 2015, vol. 47, No. 12, pp. 1411-1414.
Dwight et al. "TERT structural rearrangements in metastatic pheoschromocytomas" Endocrine-Related Cancer, 2018, vol. 25, pp. 1-9.
Peifer et al. "Telomerase activation by genomic rearrangements in high-risk neuroblastoma" Nature, Oct. 29, 2015, vol. 526, pp. 700-704.
Hansen et al. "Genetics of glioma" The Duke Glioma Handbook, Cambridge University Press, 2016, pp. 1-23.
Yang et al. "Classification based on mutations of TERT promoter and IDH characterizes subtypes in grade II/III gliomas" Neuro-Oncology 18(8), 1099-1108, 2016.

* cited by examiner

*Primary Examiner* — Kenneth R Horlick
(74) *Attorney, Agent, or Firm* — Banner & Witcoff, Ltd.

(57) ABSTRACT

The majority of glioblastomas can be classified into molecular subgroups based on mutations in the TERT promoter (TERTp) and isocitrate dehydrogenase 1 or 2 (IDH). These molecular subgroups utilize distinct genetic mechanisms of telomere maintenance, either TERTp mutation leading to telomerase activation or ATRX-mutation leading to an alternative lengthening of telomeres phenotype (ALT). However, about 20% of glioblastomas lack alterations in TERTp and IDH. These tumors, designated $TERTp^{WT}$-$IDH^{WT}$ glioblastomas, did not have well-established genetic biomarkers or defined mechanisms of telomere maintenance. The genetic landscape of $TERTp^{WT}$-$IDH^{WT}$ glioblastoma includes tumors that have chromosomal rearrangements upstream of TERT. These rearrangements define a novel molecular subgroup of glioblastoma, that is a telomerase-positive subgroup driven by TERT-structural rearrangements ($IDH^{WT}$-$TERT^{SV}$).

18 Claims, 26 Drawing Sheets

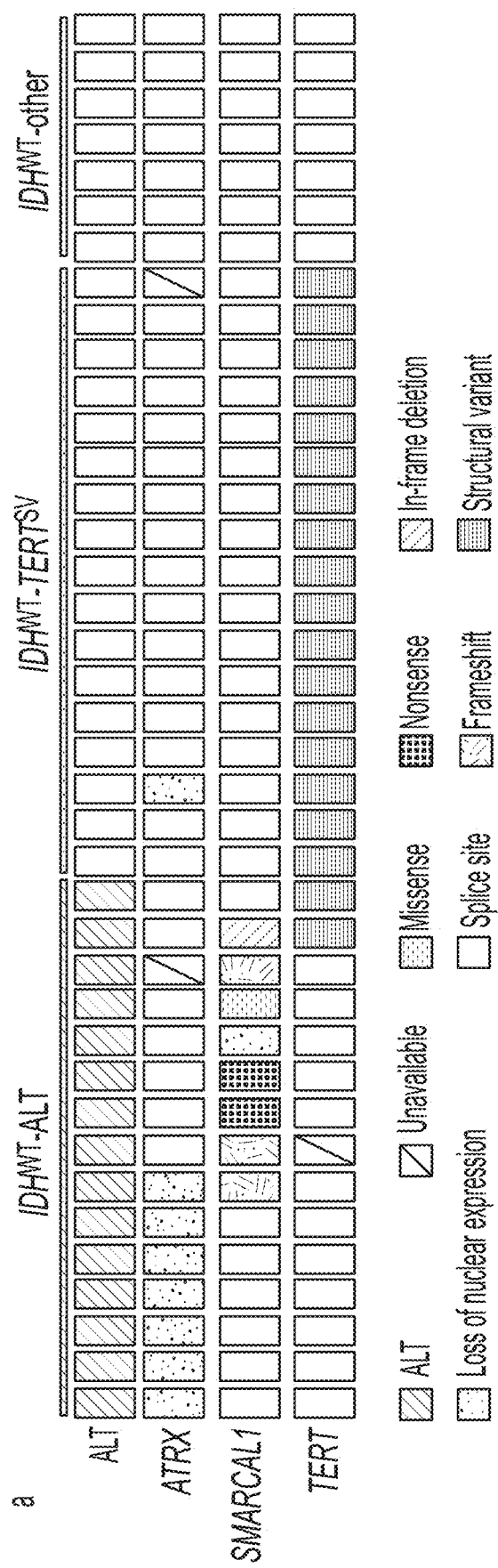
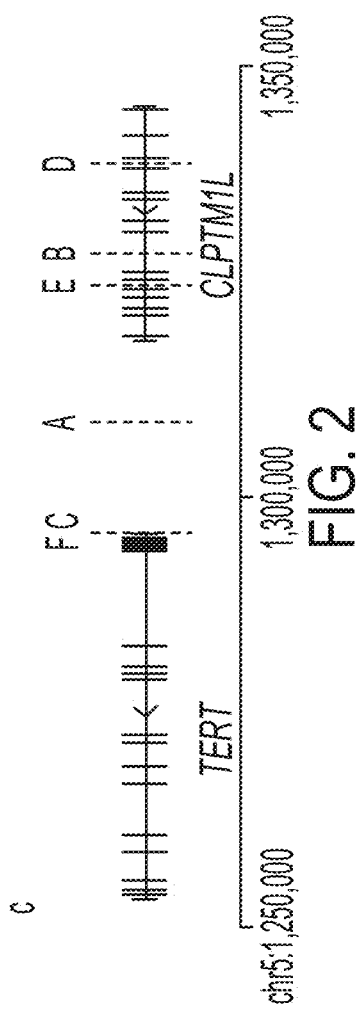
FIG. 2

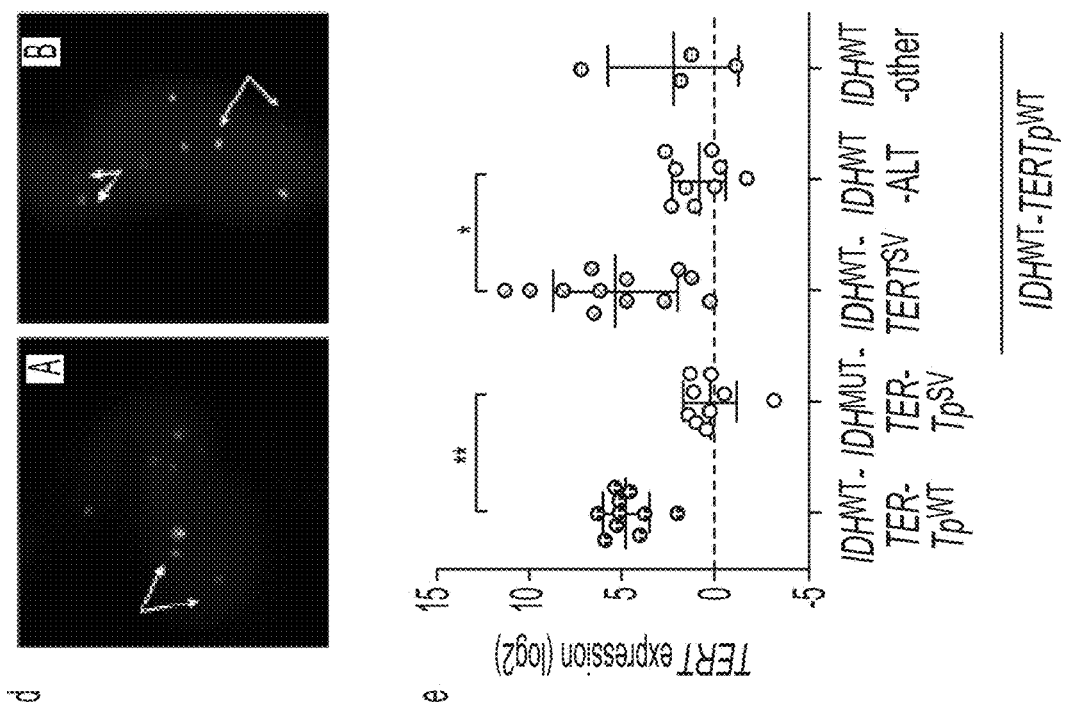
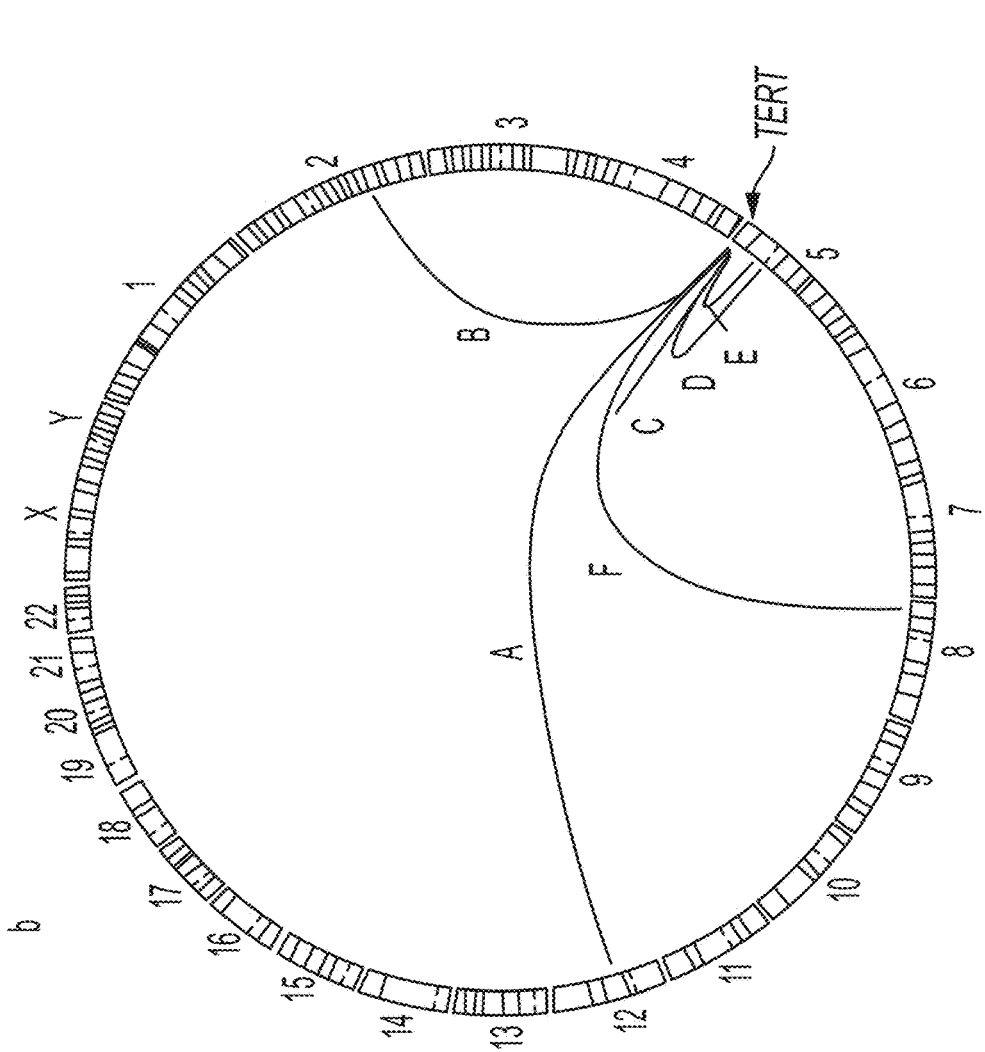
FIG. 2 Cont.

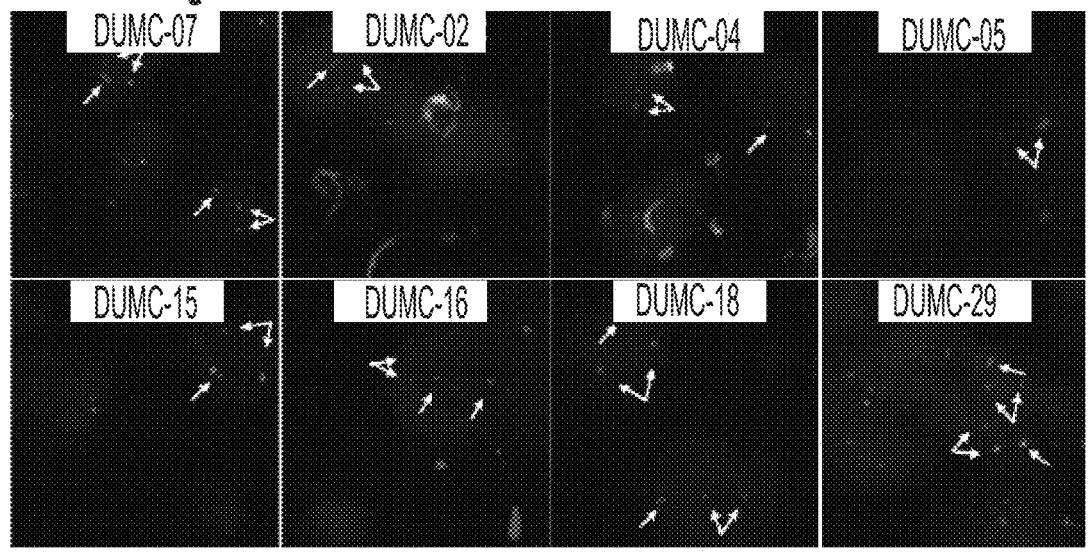
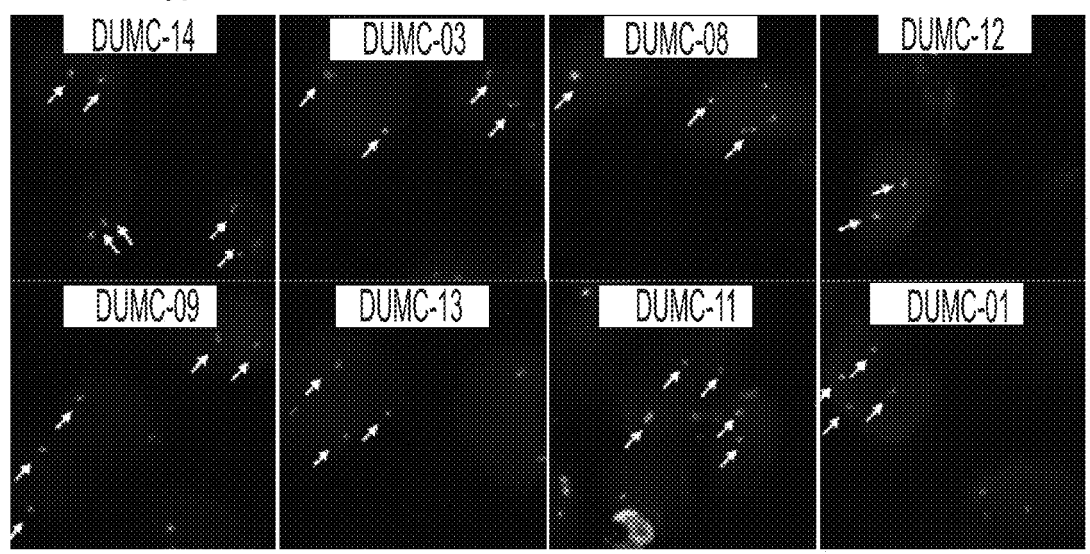
FIG. 8B

| TCGA ID | Cancer Type | Mutation | Mutation Type | CNV Status | Mutant Allele Fraction |
|---|---|---|---|---|---|
| TCGA-QC-A6FX-01 | Soft tissue sarcoma | T724M | Missense | Shallow Deletion | 17.0% |
| TCGA-DX-AB32-01 | Soft tissue sarcoma | R645C | Missense | Shallow Deletion | 40.0% |
| TCGA-JV-A5VF-01 | Soft tissue sarcoma | E803G | Missense | Shallow Deletion | 59.0% |
| TCGA-QQ-A5VB-01 | Soft tissue sarcoma | K875R | Missense | Shallow Deletion | 63.0% |
| TCGA-IW-A3M6-01 | Soft tissue sarcoma | Q145* | Nonsense | Shallow Deletion | 66.0% |
| TCGA-DX-A3U7-01 | Soft tissue sarcoma | Homozygous Deletion | | Homozygous Deletion | |
| TCGA-DX-AB2F-01 | Soft tissue sarcoma | Homozygous Deletion | | Homozygous Deletion | |
| TCGA-DX-AB2P-01 | Soft tissue sarcoma | Homozygous Deletion | | Homozygous Deletion | |
| TCGA-WK-A8XX-01 | Soft tissue sarcoma | Homozygous Deletion | | Homozygous Deletion | |
| TCGA-X6-A8C2-01 | Soft tissue sarcoma | Homozygous Deletion | | Homozygous Deletion | |

FIG. 13 anti-ATRX
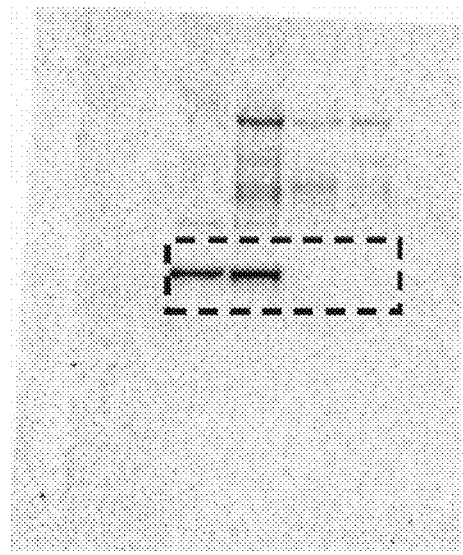
anti-DAXX
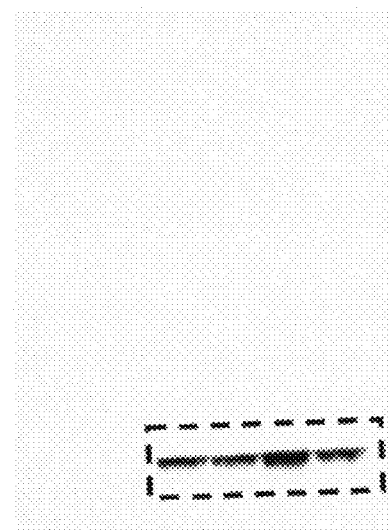
anti-SMARCAL1
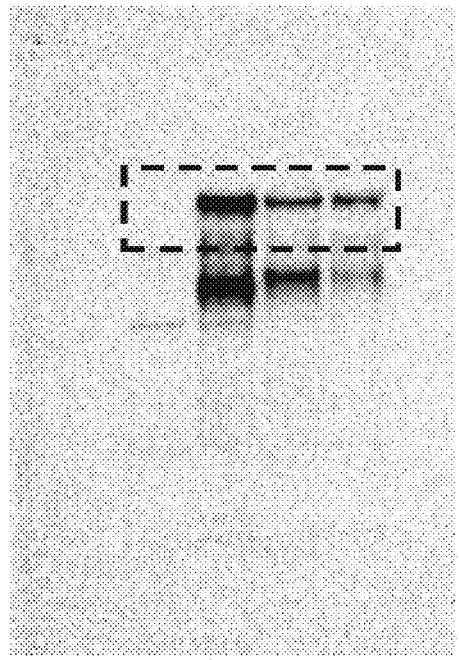
anti-GAPDH
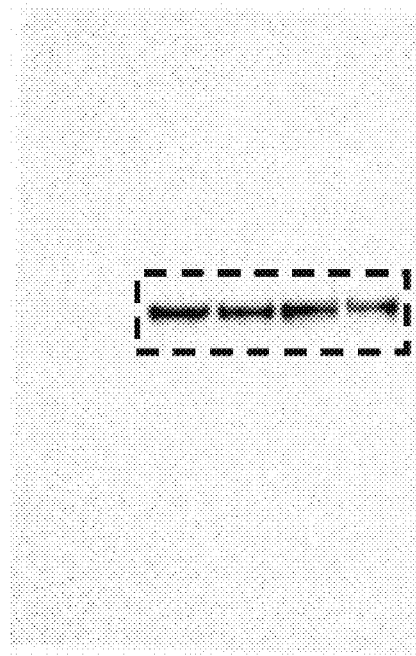
FIG. 15

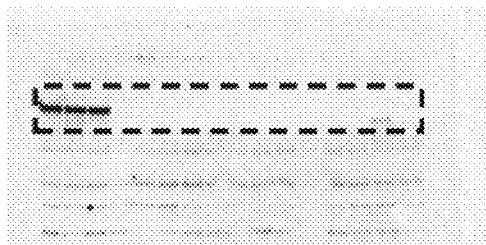
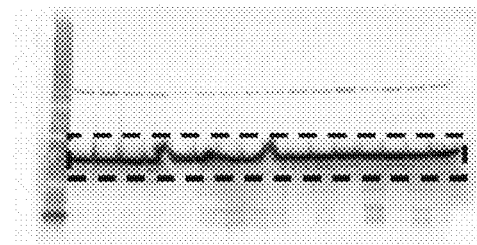
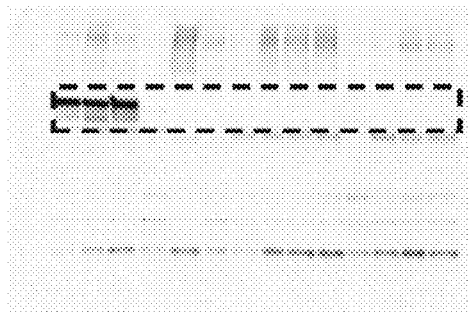
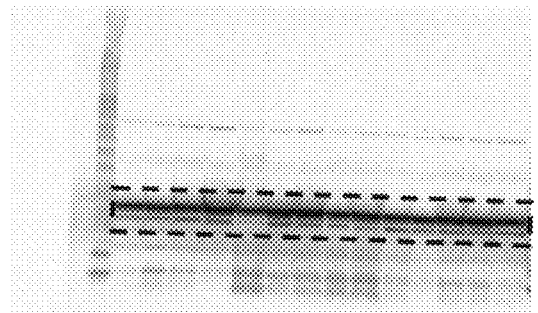
FIG. 16

DIRECTING TREATMENTS FOR GLIOBLASTOMA BASED ON IDENTIFYING A SOMATIC STRUCTURAL REARRANGEMENT UPSTREAM FROM TERT GENE

This invention was made with Government support under Federal Grant Nos. R01 CA140316 AND F30 CA206423 awarded by the NIH/NCI. The Federal Government has certain rights to this invention.

TECHNICAL FIELD OF THE INVENTION

This invention is related to the area of oncology. In particular, it relates to brain tumors.

BACKGROUND OF THE INVENTION

Glioblastoma (GBM, World Health Organization (WHO) grade IV) is the most common and deadly primary brain tumor with a median overall survival (OS) of less than 15 months despite aggressive treatment[1,2]. There is a critical need for molecular markers for GBM to improve personalized diagnosis and treatment, and for a better understanding of the underlying biology to inform the development of novel therapeutics.

SUMMARY OF THE INVENTION

According to one aspect of the invention a method of characterizing a glioma tumor of a human is provided. A glioma tumor of a human is selected. The glioma tumor comprises wild-type isocitrate dehydrogenase 1 (IDH1) gene, wild-type isocitrate dehydrogenase 2 (IDH2) gene, and wild-type promoter of telomerase reverse transcriptase gene (TERT). The glioma tumor comprises no mutant IDH1 gene, no mutant IDH2 gene, and no mutant promoter of TERT. A structural rearrangement assay is conducted on a chromosome region upstream from TERT. A structural rearrangement in the chromosome region upstream from TERT is identified in the glioma tumor of the human. The glioma tumor is assigned to a group of glioma tumors that are telomerase activated.

According to another aspect of the invention a method of characterizing a glioma tumor of a human is provided. A glioma tumor of a human is tested, to determine its genotype at codon 132 of isocitrate dehydrogenase 1 (IDH1) gene, at codon 172 of isocitrate dehydrogenase 2 (IDH2) gene, at nucleotides -124 and -146 of promoter of telomerase reverse transcriptase gene (TERT), and its structural arrangement on a region of chromosome 5 upstream from TERT. Wild-type codons 132 of IDH1, wild-type codons 172 of IDH2, wild-type nucleotides at -124 and -146 of promoter of TERT, and a somatic structural rearrangement in the chromosome region upstream from TERT of the glioma tumor of the human are identified. The glioma tumor is assigned to a group of glioma tumors that are telomerase activated based on its identified somatic structural rearrangement in the chromosome region upstream from TERT. Optionally the identified genotype of wild-type codons 132 of IDH1, wild-type codons 172 of IDH2, wild-type nucleotides at -124 and -146 of promoter of TERT is used to contribute to the assignment.

Another aspect of the invention provides a method of treating a glioma tumor of a human. A somatic structural rearrangement in the chromosome region upstream from TERT in the glioma tumor of the human is tested for and identified. The testing uses a structural rearrangement assay. The human is treated with a telomerase targeted therapy.

These and other embodiments which will be apparent to those of skill in the art upon reading the specification provide the art with means of characterizing glioblastoma tumors, in particular those which lack certain previously identified hallmarks.

BRIEF DESCRIPTION OF THE DRAWINGS

FIG. 2A-2E. Inactivating mutations in SMARCAL1 and ATRX, and rearrangements upstream of TERT are frequent in TERTpW$^T$-IDH$^{WT}$ GBMs and related to distinct telomere maintenance mechanisms. FIG. 2A: Based on ALT assessment by both telomere FISH and C-circle (dot blot), 38.5% (15/39) of TERTp$^{WT}$-IDH$^{WT}$ GBMs exhibit signs of ALT. Of these, approximately half exhibit loss of ATRX expression (IHC) and half harbor mutations in SMARCAL1, in a largely mutually exclusive manner. TERT rearrangements were identified by whole genome sequencing (N=8). Break-apart FISH was used to screen the cohort for TERT rearrangements, which were present in 50% (19/38) of all TERTp$^{WT}$-IDH$^{WT}$ GBMs. FIG. 2B: Circos plot of rearrangements identified upstream of TERT by whole genome sequencing of ALT-negative GBMs (N=8). Several cases were interchromosomal translocations (FIG. 2A, FIG. 2B, FIG. 2F), while the remaining cases were intrachromosomal (FIG. 2C, FIG. 2D, FIG. 2E). FIG. 2C: The breakpoints of the rearrangements identified by whole genome sequencing span a region in the 50 kb upstream of TERT. FIG. 2D: Examples of FISH on patient tumor tissue showing break-apart signal, indicating TERT-rearrangement. Arrows identify break-apart signals. FIG. 2E: TERT expression was assessed by rt-qPCR relative to GAPDH. IDH$^{WT}$-TERT$^{SV}$ (n=12) tumors exhibit significantly higher TERT expression than the IDH$^{WT}$-ALT subgroup (n=9, P<0.05). This is a similar trend seen among known GBM groups, where the IDH$^{WT}$-TERTp$^{MUT}$ GBMs (telomerase positive) exhibit increased TERT expression compared to IDH$^{MUT}$-TERTp$^{WT}$ (ALT positive) GBMs (P<0.01). The IDH$^{WT}$-other subgroup is ALT negative, but does not harbor detectable TERT rearrangements. One case in this group harbors MYC amplification (arrow), known to increase TERT expression due to the presence of MYC binding sites in the TERT promoter region. Error bars in FIG. 2E denote s.d. *P<0.05; **P<0.01; Kruskal ☐Wallis test with Dunn's multiple comparisons test. Three technical replicates were used for TERT mRNA expression.

FIG. 4A: The majority of mutations identified in SMARCAL1 in an expanded cohort (N=39) of TERTp$^{WT}$-IDH$^{WT}$ GBMs are likely inactivating (frameshift, nonsense). Protein domains of SMARCAL1 are shown (RBD RPA-binding domain, HARP HepA-related protein). FIG. 4B: We identified two cancer cell lines harboring inactivating mutations in SMARCAL1: D06MG (patient-derived GBM, W479X) and CAL-78 (chondrosarcoma, deletion of exons 1 ☐4). These cell lines exhibit signs of ALT, including ALT-associated PML bodies (APBs), as indicated by the co-localization of PML (immunofluorescence) and ultrabright telomere foci (FISH), and the accumulation of C-circles. FIG. 4C: Western blot confirms the absence of SMARCAL1 expression in both CAL-78 and D06MG, as well as intact expression of ATRX and DAXX. Controls include U2-OS (ATRX-negative) and HeLa (positive control). FIG. 4D: Overexpression of SMARCAL1 significantly decreased (D06MG, P<0.05; CAL-78, P<0.005) colony-forming ability as measured by percent area.

FIGS. 4E, 4F: Overexpression of SMARCAL1 dramatically reduces the appearance of ALT-associated ultrabright telomere foci relative to the GFP control (CAL-78 is shown). FIG. 4G: SMARCAL1 constructs harboring either wildtype, helicase dead (R764Q, from SIOD), mutations from the expanded cohort (R645S, del793, fs945) and recurrent mutations seen in pan-cancer data (R23C, R645C) were assayed for effects on ALT-associated C-circles. The SMARCAL1 helicase domain function is critical for suppression of C-circles, as constructs with mutations in these domains fail to fully suppress markers of ALT, compared to wildtype constructs or SMARCAL1 with mutations in the RPA-binding domain (R23C) or the 945 fs variant. Error bars in FIGS. 4D, 4F, 4G denote s.e.m. *P<0.05; P<0.01; *P<0.001; ****P<0.0001; Paired t-test (FIG. 4D, FIG. 4F) and one-way ANOVA with Dunnett's multiple comparisons test (FIG. 4G). Scale bar indicates 20 μm. Colony formation and C-circle experiments were performed in triplicate.

FIG. 5A: CRISPR/Cas9 gene editing was used to generate SMARCAL1 knockout GBM lines (U87MG and U251MG). Two guide combinations (A: 3_2 & 9_1 and B: 3_1 & 7_1) were used targeting exons 3 and 9 and 3 and 7, respectively. Clones were sequenced and validated as isogenic knockout lines by western blot (*clone c69 was excluded due to faint band). FIG. 5B: Cell lines were assessed for C-circle accumulation (by dot blot), a characteristic observed in cells using ALT for telomere maintenance. Approximately 30% of isogenic SMARCAL1 knockout GBM lines isolated in both U87MG and U251MG exhibited significantly increased levels of C-circles (U87MG: 4/12, U251MG: 3/10), as compared to the parental cell line. FIG. 5C: C-circle-positive SMARCAL1 knockout clones were assessed for the presence of ALT-associated PML bodies (APBs), as indicated by the co-localization of PML (immunofluorescence) and ultrabright telomere foci (FISH). Rare cells were identified in these C-circle-positive clones with APBs. Error bars in b denote s.e.m. P<0.01; *P<0.001; ****P<0.0001; one-way ANOVA with Dunnett's multiple comparisons test relative to parental cell line. Scale bar indicates 10 μm. C-circle experiments were performed in triplicate.

FIGS. 8A-8B. Break-apart FISH spanning TERT identifies recurrent TERT rearrangements in TERTp$^{WT}$-IDH$^{WT}$ GBM. FIG. 8A: Break-point spanning FISH probes were designed to readily detect structural variants upstream of TERT where we initially identified these events by whole genome sequencing. FIG. 8B: Break-apart FISH was performed on FFPE tissue isolated from the GBM patient tumor samples. Representative images from 8 rearranged and wild-type cases are shown. Double arrows point to break apart signals, single arrows point to fusion signals.

FIG. 9A: The CCLE database was examined for cell lines harboring mutations in SMARCAL1. We identified CAL-78, a chondrosarcoma line known to be ALT positive with intact ATRX expression. Based on Affymetrix SNP6 array data, a homozygous deletion was identified spanning exons 1-4 of SMARCAL1. FIG. 9B: We validated the deletion of exons 1-4 in CAL-78 (including the 5' UTR) by PCR and Sanger sequencing, using HeLa as a control. FIG. 9C: Compared to other cell lines, CAL-78 shows both deletion and absent mRNA expression of SMARCAL1. FIG. 9D: Sanger sequencing of the D06MG cell line reveals a homozygous W479X mutation in SMARCAL1.

FIG. 10C: There was a significant reduction in the colony area and intensity for D06MG (P<0.05) and CAL-78 (P<0.005) in the SMARCAL1 rescue as compared to the control (GFP). Error bars in c denote s.e.m. *P<0.05; **P<0.05; Paired t-test.

FIG. 11A: We examined pancancer data (cBioportal) for mutations and homozygous deletions. FIG. 11B: Recurrently-mutated loci included R23 and a cluster in the SNF2 helicase domain at R645. R23C is located in the RPAbinding domain and forms hydrogen bonds with RPA. R645C is in the ATP-binding helicase domain (also SNF2 N-terminal domain and putative nuclear localization signal domain) and is a known alteration in SIOD. Additionally, from our validation cohort, we identified ALT-positive cases with R645S, del793 and fs945 mutations. FIG. 11C: Mutagenized constructs with each of these variants were generated and delivered by lentivirus for constitutive expression in D06MG and CAL-78. Western blot analysis shows that the constructs are expressed at similar levels in these cell lines and similar to a control cell line (HeLa).

FIG. 12A-12-B. Generation of SMARCAL1 knockout glioblastoma cell lines using CRISPR/Cas9-mediated gene editing. FIG. 12A: Guides were designed to target the coding region of SMARCAL1 with low off-targets and high cutting efficiency. The guides were tested using the Surveyor nuclease assay after transfecting HEK293FT cells with pX458 (spCas9) and the relevant sgRNA. All guides readily introduced indels (>20%). FIG. 12B: Two guide combinations (A: 3_2+9_1 and B: 3_1+7_1) were delivered to U87MG and U251MG. After transfection, cells were GFP-sorted and single-cell cloned and expanded. Deletion-spanning qPCR was performed to readily identify clones with allele deletion in SMARCAL1. These lines were then sequenced and validated as isogenic knockout lines by Western blot. Overall, more than ten isogenic SMARCAL1 knockout lines were generated in both U87 (11 total) and U251 (12 total). Clone c69* was excluded from further analysis due to the presence of a faint band by immunoblot.

FIG. 13. SMARCAL1 mutations are present in soft tissue sarcoma. We examined a recent TCGA sequencing study on many sarcoma subtypes and found several homozygous deletions and potentially inactivating variants, as many had concurrent shallow deletion and mutations present in the helicase domains.

FIG. 15. Original western blots for examining SMARCAL1 expression in mutant cell lines. Shown are the original blots for ATRX, DAXX, SMARCAL1, and GAPDH expression in HeLa, U2-OS, D06MG, and CAL-78. The images are cropped on the right side as unrelated samples were run on the same gel.

FIG. 16. Original western blots for SMARCAL1 expression in isogenic knockout cell lines. Shown are the original blots for SMARCAL1 and GAPDH expression in U87MG and U251MG SMARCAL1 knockouts. The images for U87MG is cropped on the right side as unrelated samples were run on the same gel.

DETAILED DESCRIPTION OF THE INVENTION

Figure 1:
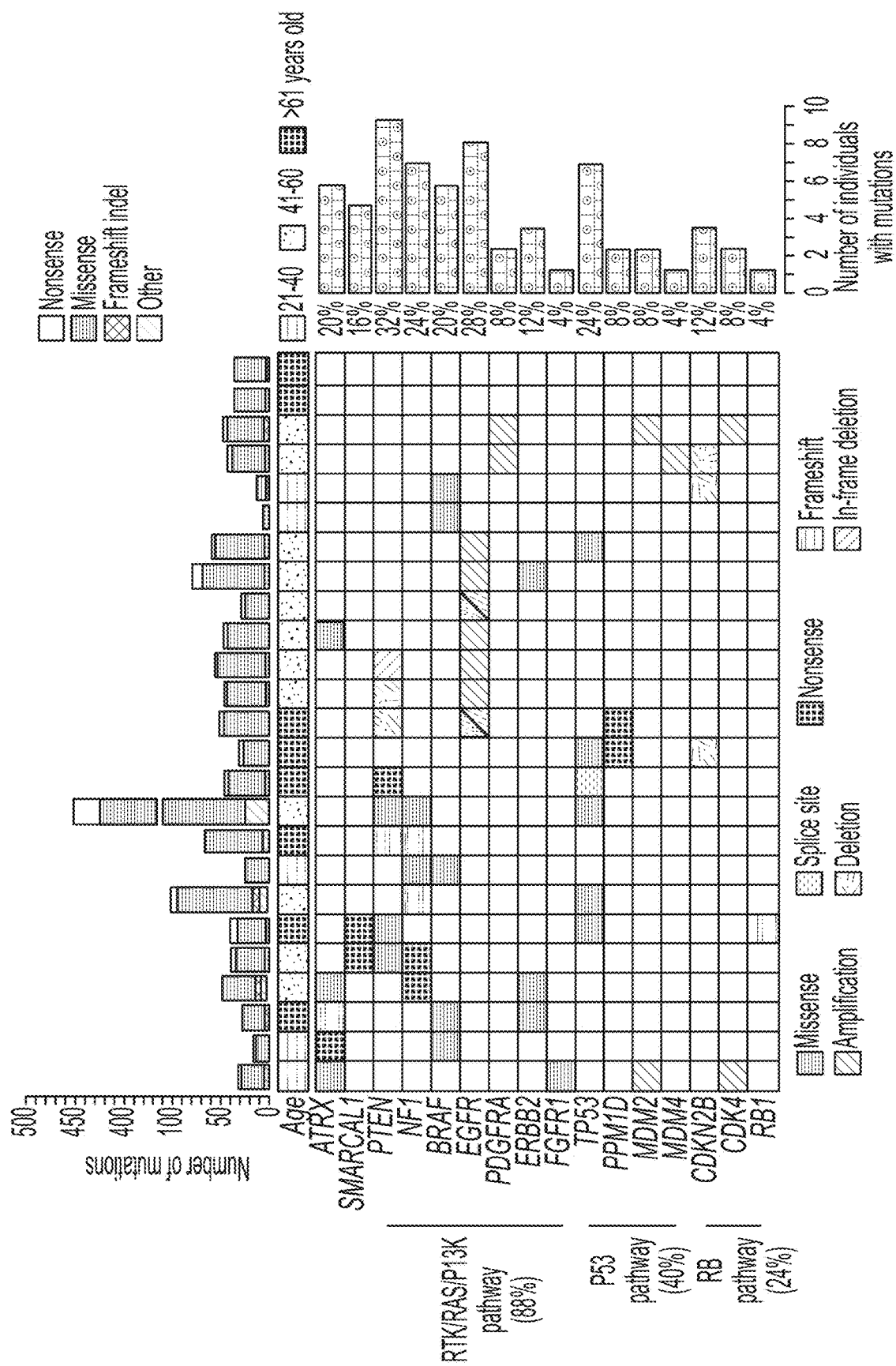
FIG. 1. The mutational landscape of somatic coding alterations in TERTp$^{WT}$-IDH$^{WT}$ GBM. Whole exome sequencing was performed on TERTp$^{WT}$-IDH$^{WT}$ GBMs (N=25). Recurrently mutated pathways identified included the RTK/RAS/PI3K (88%), P53 (40%), and RB (24%) pathways. Somatic mutation rates per case are shown with corresponding patient age (top). Recurrently mutated genes displayed determined to be significantly mutated (IntOgen algorithm, P<0.05, n≥2) are shown, as well as select lower frequency genes that are recurrently mutated in glioma or known oncogenes/tumor suppressors in the pathways shown. The mutation frequency of each gene is shown (right) as a percentage of the total cohort.

The inventors have developed a comprehensive molecular analysis of ~20% of GBMs that lack established genetic biomarkers or defined mechanisms of telomere maintenance[3]. These are aggressive tumors that are known as $TERTp^{WT}$-$IDH^{WT}$ GBMs, a largely unknown set, as they lack mutations in the most commonly used biomarkers, isocitrate dehydrogenase 1 and 2 (IDH)' and the promoter region of telomerase reverse transcriptase (TERTp)[5-7].

Proper characterization of glioblastomas permits proper treatments, diagnoses, and predictions of survival time. These are critical for best management of glioblastoma patients. In addition, proper characterization permits its use in creating arms of clinical trials.

Testing and identification of IDH1, IDH2, and TERTp may be done before or at the same time as testing for structural rearrangements upstream of TERT on chromosome 5. There may be situations where the reverse order is desirable. Because of the very limited location and nature of IDH1, IDH2, and TERTp mutations, they are often tested and detected using a site-directed technique. These may include such techniques as polymerase chain reaction, mutation specific polymerase chain reaction, and labeled probe hybridization. Typically sequencing of the entire IDH1, IDH2, and/or TERT genes is not necessary. Somatic structural rearrangements upstream from TERT do not occur in a unique location. Some are intrachromosomal and some are extrachromsomal. The rearrangements may be inversions, duplications, or translocations. See FIG. 2B. Thus, site-specific techniques will be less helpful. Although sequencing can be used to identify rearrangements, a technique like break-apart fluorescence in situ hybridization (FISH) with probes spanning TERT can also be used with success. A break-apart signal indicates a TERT rearrangement. The two probes can be labeled with different fluors. One probe can be upstream of the gene and one within the gene and/or downstream of the gene. Breakpoints can be confirmed using a junction spanning polymerase chain reaction.

When a glioma tumor has been identified having a rearrangement upstream of TERT and optionally wild-type IDH1, IDH2, and TERTp, it is characterized as telomerase-activated. The overall survival can be determined as being better than for a glioma with $TERTp^{MUT}$ or ALT phenotype, but worse than for a glioma with an $IDH^{MUT}$ genotype. The overall survival given current data is 19.7 months. But this may be modified when other new data become available in the future.

Another situation where testing for an upstream rearrangement of TERT may be desirable is in a patient whose tumor had previously been treated with a telomerase-targeted therapy. For example, a tumor that had been found to have a TERT promoter mutation or might acquire an upstream rearrangement of TERT during treatment, or a previously present low frequency rearrangement might be selected for by the telomerase-targeted therapy.

Based on the upstream TERT rearrangement, one can prescribe or administer a telomerase-targeted therapy. Such a therapy might be a human TERT-derived peptide vaccine, for example. Alternatively, the therapy could be an antisense oligonucleotide directed to the TERT gene, TERT RNA template, or telomerase. One such oligonucleotide is imetelstat. Another option is to use a small molecule inhibitor of TERT, such as epigallocatechin-3-gallate (EGCG) or rapamycin. Some drugs inhibit telomerase as an off-target. Such drugs may be useful for treating glioma with a TERT rearrangement and include allicin, curcumin, silbinin, genistein, sulforaphane, GV1001, dasatinib, imatinib, gefitinib, nilotinib, bortezomib, 5-azacytidine, arsenic trioxide, temozolomide, suramin, troglitazone, romidepsin, vorinostat, beta-lapachone, cisplatin, melatonin, perifosine, nimesulide, auranofin, pyrimethamine, azidothymidine, octreotide ofloxacin, quinacrine, bortezomib, etoposide, and doxorubicin.

In some cases, rather than treating a glioma tumor identified as being TERT-activated by somatic rearrangement upstream of TERT, a practitioner may provide a diagnosis or prognosis. For example, a practitioner may not be the treating physician, or the patient may decline treatment. In such cases, the practitioner may provide to the patient an indication of the overall survival (time until death) that can be expected. Current data indicates that the overall survival for such tumors is 19.7 months. But, additional data and changes to treatment my change that prediction. In other cases, the practitioner may be a clinical laboratory.

TERTp and IDH mutations are routinely used clinically to facilitate diagnosis by classifying 80% of GBMs into molecular subgroups with distinct clinical courses[4-13]. Each GBM molecular subgroup also utilizes different mechanisms of telomere maintenance. The TERTp-mutant GBMs exhibit telomerase activation, due to generation of de novo transcription factor binding sites leading to increased TERT expression[5,14-16], while the IDH-mutant GBMs exhibit alternative lengthening of telomeres (ALT) due to concurrent loss-of-function mutations in ATRX[3,10,13,17-20]. Based on these patterns, genetic alterations enabling telomere maintenance are likely to be critical steps in gliomagenesis.

We used whole exome sequencing (WES) and whole genome sequencing (WGS) to define the mutational landscape of TERTp$^{WT}$-IDH$^{WT}$ GBM. We identified recurrently mutated genes and pathways in this tumor subset. Most notably, we identified somatic mutations related to mechanisms of telomere maintenance. These include recurrent genomic rearrangements upstream of TERT (50%) leading to increased TERT expression, and alterations in ATRX (21%) or SMARCAL1 (20%) in ALT-positive TERTp$^{WT}$-IDH$^{WT}$ GBMs. Somatic SMARCAL1 loss-of-function mutations are involved in ALT-mediated telomere maintenance in cancer. SMARCAL1 functions as an ALT suppressor and genetic factor involved in telomere maintenance. Finally, we identified an enrichment of several therapeutically targetable alterations in TERTp$^{WT}$-IDH$^{WT}$ GBM, including mutations in BRAF V600E (20%).

Approximately one in every five adult GBM patients have tumors that are wildtype for TERTp and IDH1/2[3,4]. TERTp$^{WT}$-IDH$^{WT}$ GBMs are a poorly understood subgroup that have been defined by an absence of common biomarkers (mutations in TERTp, IDH1/2, and 1p/19q codeletion). Here, we used genomic sequencing (WES, WGS) and characterization of telomere maintenance mechanisms to define the genetic landscape of TERTp$^{WT}$-IDH$^{WT}$ GBMs and uncover novel alterations associated with telomere maintenance in GBM.

We identified an ALT-positive subgroup of TERTp$^{WT}$-IDH$^{WT}$ GBMs, known as IDH$^{WT}$-ALT, which is made up equally of GBMs mutated in ATRX (notably without IDH or TP53 mutations) or SMARCAL1. Our study reveals a novel role for somatic recurrent loss-of-function alterations in SMARCAL1 in cancers with the ALT telomere maintenance mechanism. Another recent study[26] reported a role for SMARCAL1 in regulating ALT activity in ATRX-deficient cell lines by resolving replication stress and telomere stability[38]. Here, we show that cancers with somatic mutation of SMARCAL1 are ALT positive, and this represents, to our knowledge, the only other reported gene mutation associated with ALT other than ATRX and DAXX mutations[13]. Future studies should investigate if ATRX plays a role in the absence of SMARCAL1 expression at the telomeres in these tumors.

Figure 4:
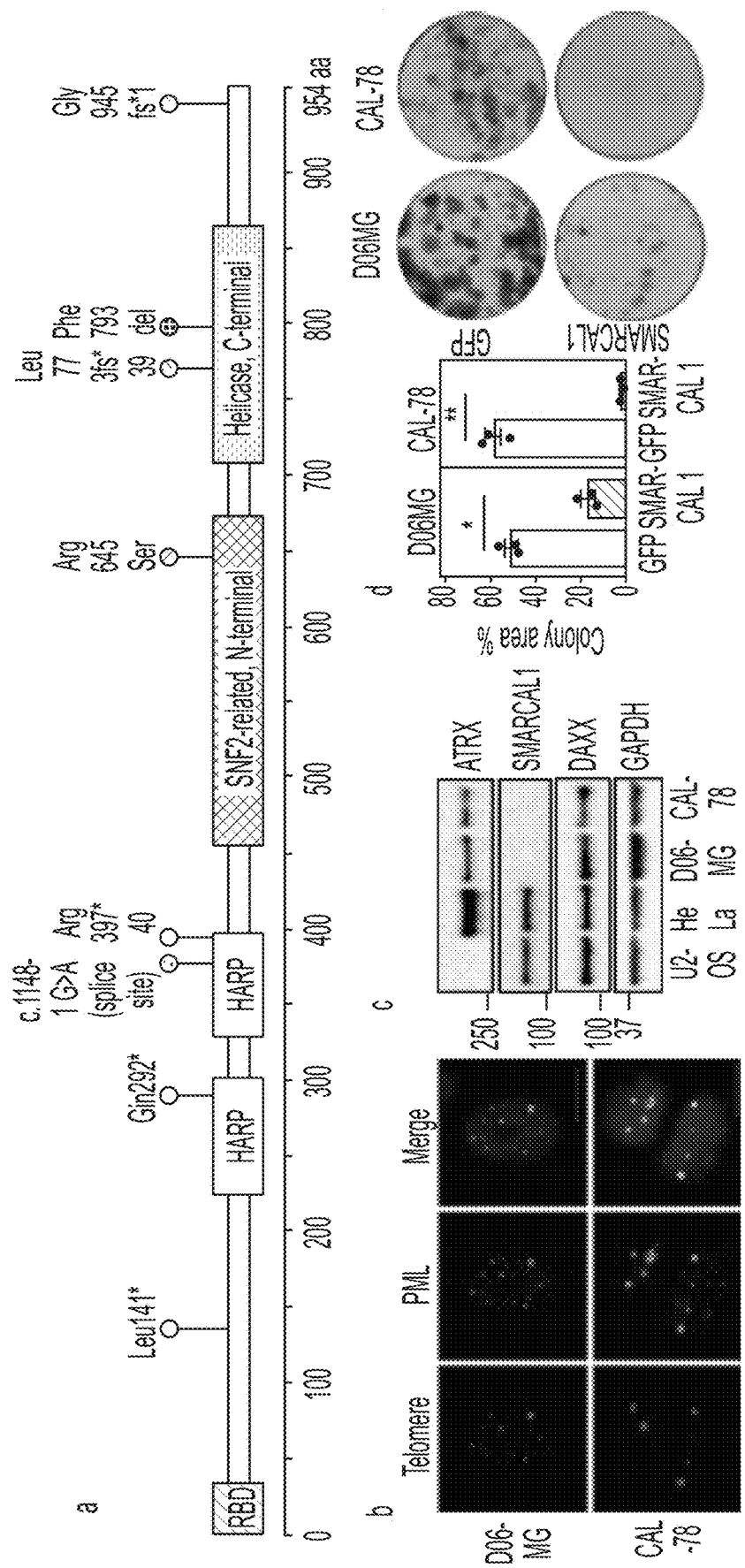
FIG. 4A-4G. Inactivating mutations in SMARCAL1 mutations cause hallmarks of ALT.
Figure 4:
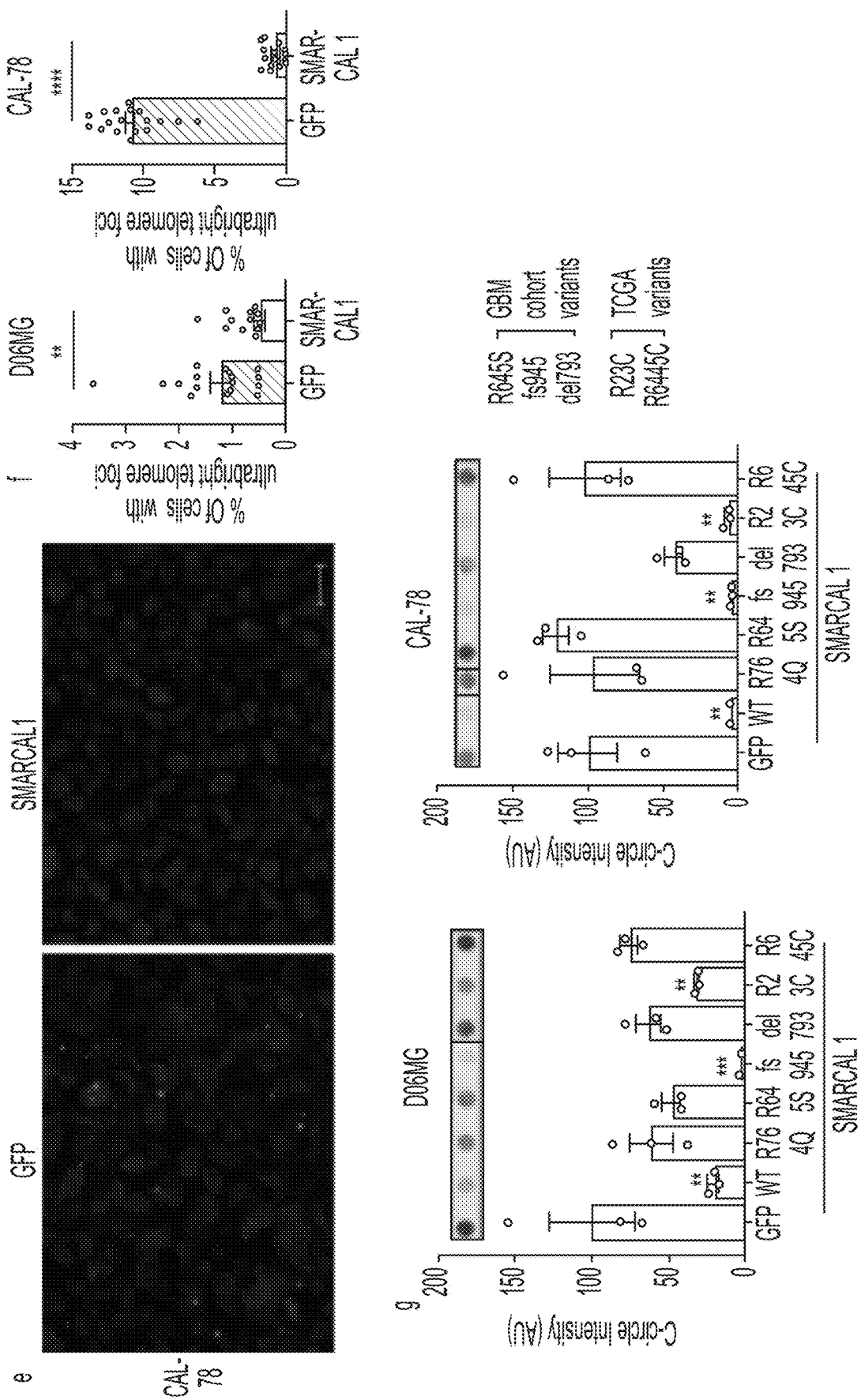

Our results demonstrate the importance of intact SMARCAL1 helicase domains in suppressing characteristics of ALT in SMARCAL1 mutant, ALT-positive cancer cell lines (FIG. 4G). These findings are consistent with a previous study[27], which used RNA interference-mediated SMARCAL1 knockdown in Hela1.3 and SMARCAL1 gene knockout in MEFs (ALT-negative cell lines with native SMARCAL1 expression) to investigate the effect of SMARCAL1 depletion on C-circle abundance. The investigators reported that SMARCAL1-mediated C-circle suppression requires intact helicase activity, and that deletion of the RPA binding domain does not affect C-circle suppression in these cell lines[27].

SMARCAL1 is recruited to sites of DNA damage and stalled replication forks by RPA, where it promotes fork repair and restart, thereby helping to maintain genome stability[24,25,39,40]. Previous work has shown that bi-allelic germline mutations of SMARCAL1 cause the autosomal-recessive disease SIOD, a rare developmental disorder characterized by skeletal dysplasia, renal failure, T-cell deficiency, and often microcephaly[41]. There is some evidence that SIOD patients have increased risk for cancer[42,43], neurologic abnormalities[44], and chromosomal instability[45]. In the context of our findings, linking SMARCAL1 alterations to the pathogenesis of ALT-positive tumors provides insights that may inform the design of therapeutics to exploit the altered replication stress response present in ALT-positive tumors. Additionally, our exome sequencing data show that SMARCAL1-mutant GBMs often have mutations in PTEN, NF1, and TP53, which may be necessary co-occurring alterations necessary for gliomagenesis. Our analysis of previous sequencing studies reveals that among diffuse gliomas, SMARCAL1 mutations appear to be absent in lower-grade gliomas (WHO grade HEM) and only present in GBMs. Furthermore, SMARCAL1 mutation is not present in the other major genetic subtypes of GBM (IDH$^{MUT}$-TERTp$^{WT}$ or IDH$^{WT}$-TERTp$^{MUT}$)[12,46,47]. SMARCAL1 somatic mutations occur in other cancer types (FIG. 11), many of which are known to exhibit ALT in a subset of tumors". We found the mutational pattern in a recent study of sarcoma of particular interest, as this tumor type commonly exhibits ALT. We identified a number of likely pathogenic alterations in SMARCAL1 in 4% of all cases, including helicase domain mutations with co-existing shallow copy number deletion, as well as tumors with homozygous deletions (FIG. 13)[480]. Additionally, the SMARCAL1-mutated ALT-positive cell line we identified in our study, CAL78, is a chondrosarcoma cell line.

We also identified recurrent TERT rearrangements in approximately half of TERTp$^{WT}$-IDH$^{WT}$ GBMs, now defined as IDH$^{WT}$-TERT$^{SV}$ GBMs. Recent studies have revealed the presence of similar structural rearrangements upstream of TERT in kidney cancer[51] and neuroblastoma[52,53]. As the exact location of the break point was variable (similar to patterns seen in other cancers[51-53]), these alterations may translocate TERT to areas of the genome with a genetic environment more permissive to increased TERT expression.

Figure 14:
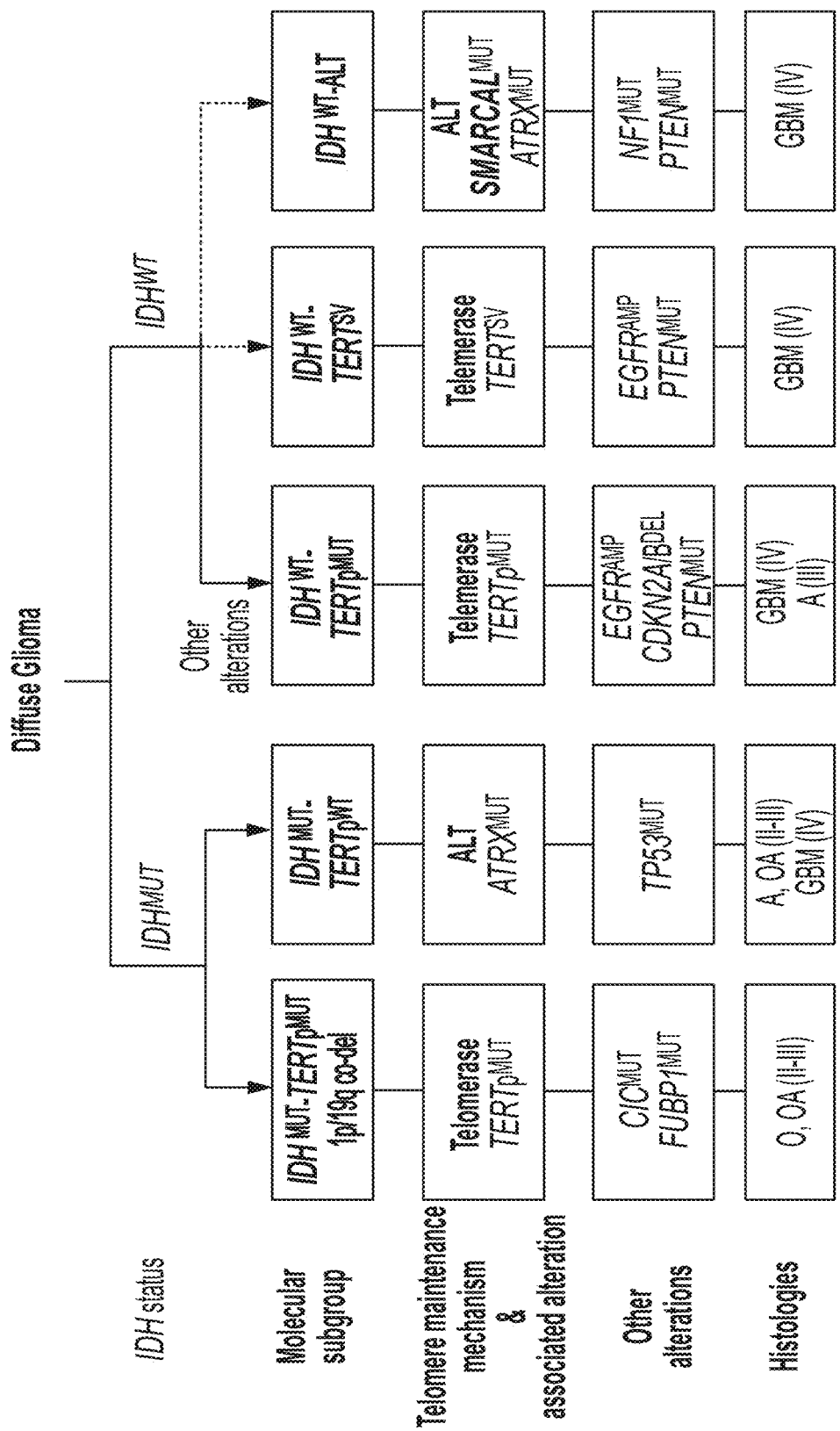
FIG. 14. Novel genetic subtypes of GBM in the overall molecular classification of adult diffuse glioma. The molecular subtypes of GBM are outlined, stratified first by IDH status, then by markers including TERTp mutation, 1p/19q co-deletion, and now TERT rearrangement ($IDH^{WT}$-$TERT^{SV}$) and SMARCAL1 or ATRX mutation ($IDH^{WT}$-ALT). The two new genetic subtypes of GBM, $IDH^{WT}$-$TERT^{SV}$ and $IDH^{WT}$-ALT (red arrows), have novel genetic alterations associated with telomere maintenance.

Taken together, we have delineated two new genetically defined GBM subgroups, IDH$^{WT}$-TERT$^{SV}$ and IDH$^{WT}$-ALT. Similar to the established IDH$^{MUT}$ and TERTp$^{MUT}$ genetic subgroups of GBM[4-8,10], the IDH$^{WT}$-ALT and IDH$^{WT}$-TERT$^{SV}$ genetic subgroups exhibit recurrent and distinct genetic alterations leading to either ALT-mediated or telomerase-mediated mechanisms of telomere maintenance (FIG. 14).

We also observed truncating mutations in the putative oncogene PPM1D, similar to previous observations of PPM1D mutations in brainstem gliomas[11], suggesting that PPM1D is a candidate driver gene in a subset of TERTp$^{WT}$-IDH$^{WT}$ GBMs. In the TCGA LGG and GBM studies, PPM1D truncating mutations were rare (<1% of cases); however, gain or amplification occurred in 5.7% and 12.5% of cases, respectively[23,34,46]. PPM1D alterations therefore appear to be present both in brainstem gliomas and less frequently in supratentorial gliomas.

Finally, we identify clinically actionable alterations through sequencing in this cohort, including BRAF V600E mutations. While BRAF is frequently altered in pediatric gliomas, it is uncommon in adult gliomas (0.7–2%)[46,47,54]. In our study, we identified recurrent BRAF V600E alterations primarily in adult TERTp$^{WT}$-IDH$^{WT}$ GBM patients 30 years old or younger. These results suggest that BRAF mutations may be suspected in young adult TERTp$^{WT}$-IDH$^{WT}$ GBM patients, which provides an opportunity to use molecular diagnostic markers and targeted BRAF V600E/MEK blockade, which has shown promise in pre-clinical models of astrocytoma[55,56] and in pediatric and adult patients with BRAF-mutant tumors[57].

These studies identify novel biomarkers that can be used to objectively define TERTp$^{WT}$-IDH$^{WT}$ GBM tumors and also identify somatic SMARCAL1 loss-of-function mutations with the ALT phenotype in human cancers.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element "means at least one element and can include more than one element.

"About" is used to provide flexibility to a numerical range endpoint by providing that a given value may be "slightly above" or "slightly below" the endpoint without affecting the desired result.

The use herein of the terms "including," "comprising," "or "having," "and variations thereof, is meant to encompass the elements listed thereafter and equivalents thereof as well as additional elements. Embodiments recited as "including," "comprising/* or "having" certain elements are also contemplated as "consisting essentially of" and "consisting of" those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "biomarker" refers to a naturally occurring biological molecule present in a subject at varying concentrations useful in predicting the risk or incidence of a disease or a condition, such as glioblastoma. For example, the biomarker can be a protein, amino acid(s), branched chain keto acids, and/or other conventional metabolites that present in higher or lower amounts in a subject at risk for, or suffering from, glioblastoma. The biomarker may also include nucleic acids, ribonucleic acids, or a polypeptide used as an indicator or marker for glioblastoma in the subject. A biomarker may also comprise any naturally or non-naturally occurring polymorphism (e.g., single-nucleotide polymorphism [SNP]) present in a subject that is useful in predicting the risk or incidence of glioblastoma. In some embodiments, the biomarker comprises SMARCAL1.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises glioblastoma. In certain embodiments, the cancer comprises a glioblastoma having the TERTp$^{WT}$-IDH$^{WT}$ phenotype.

As used herein, the term "treating" or "treatment, "refers to the management and care of a subject for the purpose of combating and reducing cancer, such as glioblastoma. Treating may reduce, inhibit, ameliorate and/or improve the onset of the symptoms or complications, alleviating the symptoms or complications of the tumor, or eliminating cancer (e.g., glioblastoma). As used herein, the term "treatment" is not necessarily meant to imply cure or complete abolition of the disease. Treatment may refer to the inhibiting or slowing of the progression of the cancer (e.g., glioblastoma), reducing the incidence of cancer (e.g., glioblastoma), or preventing additional progression of cancer (e.g., glioblastoma).

As used herein, the term ameliorate, amelioration, improvement or the like refers to a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated.

The term effective amount or therapeutically effective amount refers to an amount sufficient to effect beneficial or desirable biological and/or clinical results.

As used herein, the term subject and patient are used interchangeably herein and refer to both human and nonhuman animals. The term nonhuman animals of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In other embodiments, the subject comprises a human suffering from, or at risk of developing, cancer. In certain embodiments, the subject comprises a human suffering from, or at risk of developing, glioblastoma.

The term biological sample as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample comprises a serum sample or blood. A biological sample may be obtained directly from a subject (e.g., by blood or tissue sampling) or from a third party (e.g., received from an intermediary, such as a healthcare provider or lab technician).

Unless otherwise defined, all technical terms used herein have the same meaning as commonly understood by one of ordinary skill in the art to which this disclosure belongs.

The present disclosure provides, in part, biomarkers for glioblastomas, and more particularly, glioblastomas having the TERTp$^{WT}$-IDH$^{WT}$ phenotype. These biomarkers permit one to predict, treat, prognose, and/or diagnose glioblastomas having the TERTp$^{WT}$-IDH$^{WT}$ phenotype. Further, the biomarkers provided here are useful to aid in predicting, treating, prognosing and/or diagnosing those glioblastomas having the alternative lengthening of telomeres (ALT) phenotype.

In one aspect, the disclosure provides a panel of non-invasive biomarkers for glioblastomas comprising, consisting of, or consisting essentially of SWI/SNF-related, matrix-associated, actin-dependent regulator of chromatin, subfamily A-like 1 (SMARCAL1) which are associated with glioblastomas. In some embodiments, the glioblastoma comprises the TERTp$^{WT}$-IDH$^{WT}$ phenotype. In other embodiments, the glioblastoma comprises the ALT phenotype.

In yet another aspect, the disclosure provides a method of detecting a panel of biomarkers associated with glioblastomas in a subject. The method comprises obtaining a sample from a subject; detecting at least one biomarker related to glioblastomas in a sample obtained from the subject; in which the presence of the biomarker is indicative of a glioblastoma. In some embodiments, the biomarker comprises SMARCAL1. In other embodiments, the presence of SMARCAL1 is indicative of a glioblastoma having the TERTp$^{WT}$-IDH$^{WT}$ phenotype. In yet another embodiment, the presence of SMARCAL1 is indicative of a glioblastoma having the ALT phenotype.

In other embodiments, the biological sample is selected from the group consisting of tissues, cells, biopsies, blood, lymph, serum, plasma, urine, saliva, mucus, and tears. In one embodiment, the sample comprises a serum sample or blood sample. In some further aspects, the method further comprises diagnosing the patient with glioblastoma. The method allows for the diagnosis without a biopsy or other invasive techniques.

In yet another aspect, a method of diagnosing or prognosing glioblastoma in a subject, wherein the method comprises, consists of, or consists essentially of obtaining a sample from a subject, detecting at least one, biomarker specific for glioblastomas in a sample obtained from the subject; in which the presence of the biomarker is indicative of a glioblastoma. In some embodiments, the biomarker comprises SMARCAL1. In other embodiments, the presence of SMARCAL1 is indicative of a glioblastoma having the TERTp$^{WT}$-IDH$^{WT}$ phenotype. In yet another embodiment, the presence of SMARCAL1 is indicative of a glioblastoma having the ALT phenotype.

In yet another aspect, the present disclosure provides a kit for detecting glioblastomas in a subject comprising means for detecting at least one biomarker as described herein in a sample.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1 — Methods

Sample Preparation and Consent

All patient tissue and associated clinical information were obtained with consent and approval from the Institutional Review Board from The Preston Robert Tisch Brain Tumor Center BioRepository (accredited by the College of American Pathologists). Adult GBM tissues were defined as WHO grade IV gliomas diagnosed after 18 years of age. Tissue sections were reviewed by board-certified neuropathologists to confirm histopathological diagnosis, in accordance with WHO guidelines, and select samples with ≥70% tumor cellularity by hematoxylin and eosin (H&E) staining for subsequent genomic analyses. A total of 25 GBMs were used for WES, and 9 for WGS. Two cases included in this study have previously been sequenced by WES[12], and Sanger sequencing for TERT promoter and IDH1/2 mutational status for 240 GBMs was used to identify candidate TERT/IDH wildtype tumors[4]. Patient diffuse glioma tumor samples from Duke University Hospital used in this study were diagnosed between 1984 and 2016.

DNA and RNA Extraction

DNA and RNA were extracted from homogenized snap-frozen tumor tissue using the QIAamp DNA Mini Kit (QIAGEN) and RNeasy Plus Universal Mini Kit (QIAGEN) per manufacturer's protocols.

Quantitative RT-PCR

Reverse transcription was performed using 1–5 μg of total RNA and the RNA to complementary DNA (cDNA) EcoDry Premix (Clontech). RT-PCR for TERT expression was performed on generated cDNA in triplicate using the KAPA SYBR FAST (Kapa Biosystems) reagent and the CFX96 (Bio-Rad) for thermal cycling and signal acquisition. The ΔΔCt method (CFX Manager) was used to determine normalized expression relative to GAPDH expression. Primers and protocols are available on-line at Nature Communications as the supplementary data associated with the article at volume 9, page 2087.

Whole Exome Sequencing

Sample library construction, exome capture, next-generation sequencing, and bioinformatic analyses of tumors and normal samples were performed at Personal Genome Diagnostics (PGDX, Baltimore, Md.) as previously described[58]. In brief, genomic DNA from tumor and normal samples was fragmented, followed by end-repair, A-tailing, adapter ligation, and polymerase chain reaction (PCR). Exonic regions were captured in solution using the Agilent SureSelect approach according to the manufacturer's instructions (Agilent, Santa Clara, Calif.). Paired-end sequencing, resulting in 100 bases from each end of the fragments, was performed using the HiSeq2500 next-generation sequencing instrument (Illumina, San Diego, Calif.). Primary processing of sequence data for both tumor and normal samples was performed using Illumina CASAVA software (v1.8). Candidate somatic mutations, consisting of point mutations, small insertions, and deletions, were identified using VariantDx across the regions of interest. VariantDx examined sequence alignments of tumor samples against a matched normal while applying filters to exclude alignment and sequencing artifacts. Specifically, an alignment filter was applied to exclude quality failed reads, unpaired reads, and poorly mapped reads in the tumor. A base quality filter was applied to limit inclusion of bases with a reported phred quality score of >30 for the tumor and >20 for the normal samples. A mutation in the tumor was identified as a candidate somatic mutation only when: (i) distinct paired reads contained the mutation in the tumor; (ii) the number of distinct paired reads containing a particular mutation in the tumor was at least 10% of the total distinct read pairs; (iii) the mismatched base was not present in >1% of the reads in the matched normal sample; and (iv) the position was covered by sequence reads in both the tumor and normal DNA (if available). Mutations arising from misplaced genome alignments, including paralogous sequences, were identified and excluded by searching the reference genome. Candidate somatic mutations were further filtered based on gene annotation to identify those occurring in protein coding regions. Finally, mutations were filtered to exclude intronic and silent changes, while mutations resulting in missense mutations, nonsense mutations, frameshifts, or splice site alterations were retained. Amplification analyses were performed using a Digital Karyotyping approach through comparison of the number of reads mapping to a particular gene compared to the average number of reads mapping to each gene in the panel. IntOgen analysis was used to identify candidate driver genes. DUMC-14 was excluded from this initially as it had high levels of mutations relative to the rest of the cohort. Candidate drivers were included if they were recurrently mutated (n≥2, separate cases) and P<0.05 (by OncodriveFM or OncodriveCLUST). Alignments were done to hg18.

Whole Genome Sequencing

The quality of DNA for WGS was assessed using the Nanophotometer and Qubit 2.0. Per sample, 1 μg of DNA was used as input for library preparation using the Truseq Nano DNA HT Sample Prep kit (Illumina) following the manufacturer's instructions. Briefly, DNA was fragmented by sonication to a size of 350 bp, and then DNA fragments were endpolished, A-tailed, and ligated with the full-length adapter for Illumina sequencing with further PCR amplification. PCR products were purified (AMPure XP) and libraries were analyzed for size distribution by the 2100 Bioanalyzer (Agilent) and quantified by real-time PCR. Clustering of the index-coded samples was performed on a cBot Cluster Generation System using the HiSeq X HD PE Cluster Kit (Illumina), per manufacturer's instructions. Libraries were then sequenced on the HiSeq X Ten and 150 bp paired-end reads were generated. Quality control was performed on raw sequencing data. Read pairs were discarded if: either read contained adapter contamination, more than 10% of bases were uncertain in either read, or the proportion of low-quality bases was over 50% in either read. Burrows☐Wheeler Aligner[59] (BWA) was used to map the paired-end clean reads to the human reference genome (hg19). After sorting with samtools and marking duplicates with Picard, the resulting reads were stored as BAM files. Somatic single-nucleotide variants were detected using muTect[60] and somatic InDels were detected using Strelka[61]. Copy number variations were identified using control-FREEC[62]. Genomic rearrangements were identified using Delly[30] (v0.7.2). ANNOVAR[63] was used to annotate variants identified.

Break-Apart FISH for TERT Rearrangements

Matched formalin-fixed, paraffin-embedded (FFPE) slides were received with one set H&E stained. The tumor location was identified and marked on the slide so that tumor-specific regions could be analyzed. The unstained slides were then aligned with the H&E-stained slides so that potential rearrangements in the tumor zone could be analyzed. Break-apart probes were designed to span TERT, with BAC clones mapped (hg19) to chr5: 816,815☐ 1,195,694 (green) and chr5: 1,352,987☐1,783,578 (orange) and directly labeled. The break-apart probe set was manufactured with the above design and was first tested on human male metaphase spreads. The probe and the sample were denatured together at 72° C. for 2 min followed by hybridization at 37° C. for 16 h. Slides were then washed at 73° C. for 2 min in 0.4×SSC/0.3% IGEPAL followed by a 2-min wash at 25° C. for 2 min in 2×SSC/0.1% IGEPAL. Slides were briefly air-dried in dark, applied DAPI-II, and visualized under fluorescence microscope. For FFPE tissue sections, the following pretreatment procedure was used. The sections were first aged for 30 min at 95° C., deparaffinized in Xylene, dehydrated in 100% ethanol, and air-dried. The slides with the sections were then incubated at 80° C. for 1 h and then treated with 2 mg/ml pepsin in 0.01 N HCl for 45 min. Slides were then briefly rinsed with 2×SSC, passed through ethanol series for dehydration, dried, and used for hybridization. The probe and the sample were denatured together at 83° C. for 5 min followed by hybridization at 37° C. for 16 h. Slides were then washed at 73° C. for 2 min in 0.4×SSC/0.3% IGEPAL followed by a 2-min wash at 25° C. in 2×SSC/0.1% IGEPAL. Slides were briefly air-dried in dark, applied DAPI-II, and visualized under fluorescence microscope. Note that a 5% break-apart signal pattern was arbitrarily considered to be the cut-off for a ☐Rearrangement☐ result as the probe is not formally validated on solid tumor tissue at Empire Genomics.

Cell Culture

CAL-78 was purchased directly from the Deutsche Sammlung von Mikroorganismen and Zellkulturen (DSMZ) and was cultured using RPMI-1640 with 20% fetal bovine serum (FBS). U87, U2-OS and HeLa were purchased from the Duke Cell Culture Facility (CCF), and were cultured with Dulbecco's modified Eagle's medium (DMEM)/F12, McCoy's 5A, and DMEM-HG, respectively, all with 10% FBS. U251MG was a generous gift from the laboratory of A.K.M and was cultured with RPMI-1640 with 10% FBS. D06MG is a primary GBM cell line from resected tumor tissue and was cultured with Improved MEM, Zinc option media, and 10% FBS. All cell lines were cultured with 1% penicillin's streptomycin. Cell lines were authenticated (Duke DNA Analysis facility) using the GenePrint 10 kit (Promega) and fragment analysis on an ABI 3130xl automated capillary DNA sequencer.

CRISPR/Cas9-Mediated SMARCAL1 Genetic Targeting

Figures 12A, 12B:
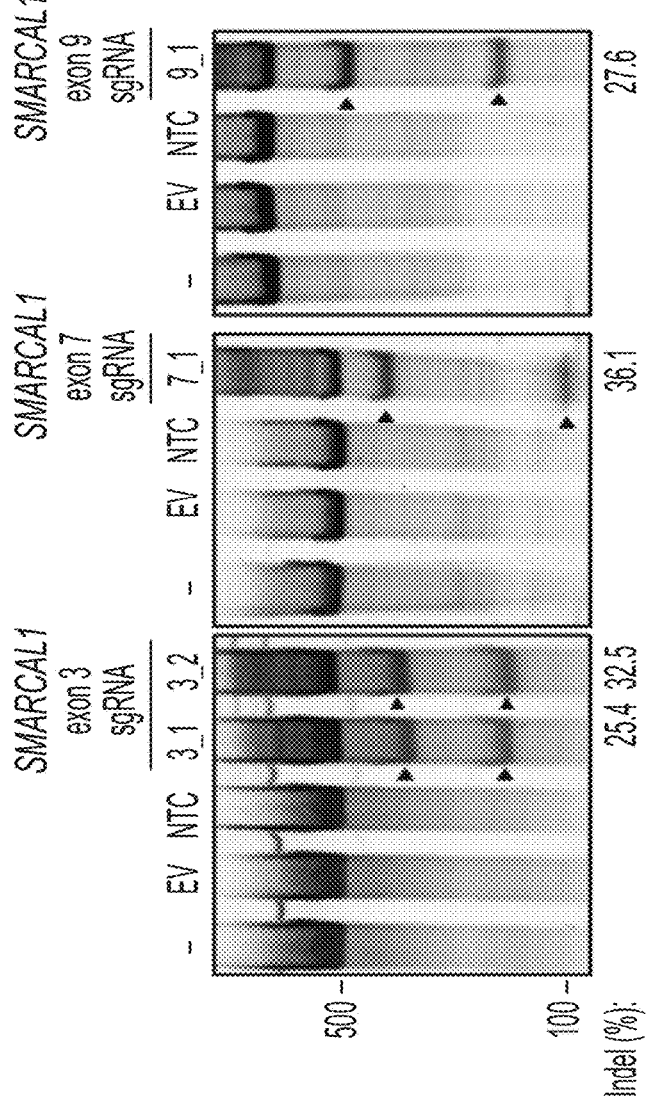

CRISPR guides were designed for minimal off-targets and maximum on-target efficiency for the coding region of SMARCAL1 using the CRISPR MIT[64] (http://crispr.mit.edu) and the Broad Institute sgRNA Design Tools[65] (http://portals.broadinstitute.org/gpp/public/analysis-tools/sgrna-design). Complementary oligonucleotides encoding the guides were annealed and cloned into pSpCas9(BB)-2A-GFP (PX458), which was a gift from Feng Zhang (Addgene plasmid #48138)[37]. PX458 contains the cDNA encoding *Streptococcus pyogenes* Cas9 with 2A-EGFP. Negative controls included the parental lines, transfection with empty vector PX458 (no guide cloned), and with PX458-sgNTC[66]. Candidate guides were first tested in HEK293FT by transfecting cloned PX458-sgRNA constructs with lipofectamine 2000 (Life Technologies) according to the manufacturer's guidelines and harvesting DNA from cells 48 h later. These constructs were assessed (i) individually for indel percentage in HEK293FT the Surveyor Mutation Detection Kit (IDT) and (ii) in various combinations for inducing deletions to facilitate gene inactivation and qPCR-based screening for knockout clones (primers and program listed in Supplementary Data available on-line at Nature Communications as the supplementary data associated with the article at volume 9, page 2087). Two guides were used to facilitate knockout of SMARCAL1, named sgSMARCAL1 A, which targeted exons 3 and 9 (3_2, 7_1) and B, which targeted exons 3 and 7 (3_1, 7_1). The cell lines U251 and U87 were transfected with Lipofectamine 3000 (Life Technologies) and Viafect (Promega), respectively, and GFP-positive cells were FACS-sorted (Astrios, Beckman Coulter, Duke Flow Cytometry Shared Resource) and diluted to single clones in 96-well plates. Negative control transfected lines (PX458 empty vector and PX458-sgNTC) were not single cell cloned after sorting. Clones were expanded over 2 to 3 weeks and DNA was isolated by the addition of DirectPCR lysis Reagent (Viagen) with proteinase K (Sigma-Aldrich) and incubation of plates at 55° C. for 30 min, followed by 95° C. for 45 min. Then, 1 µl of crude lysate was used as a template for junction-spanning qPCR (to detect dual-sgRNA induced deletion products) with KAPA SYBR FAST (KAPA Biosystems). The junction-spanning amplicon was detected by qPCR signal, using the parental (not transfected) line as a negative control. The targeted exons and junction products were sequenced to validate the presence of indels. Clones were then expanded further and screened by western blot to ensure the absence of SMARCAL1 protein expression (FIG. 12). All relevant programs and primers are listed in Supplementary Data 14-15 available on-line at Nature Communications as the supplementary data associated with the article at volume 9, page 2087.

Lentiviral Expression of SMARCAL1

Figure 11A:
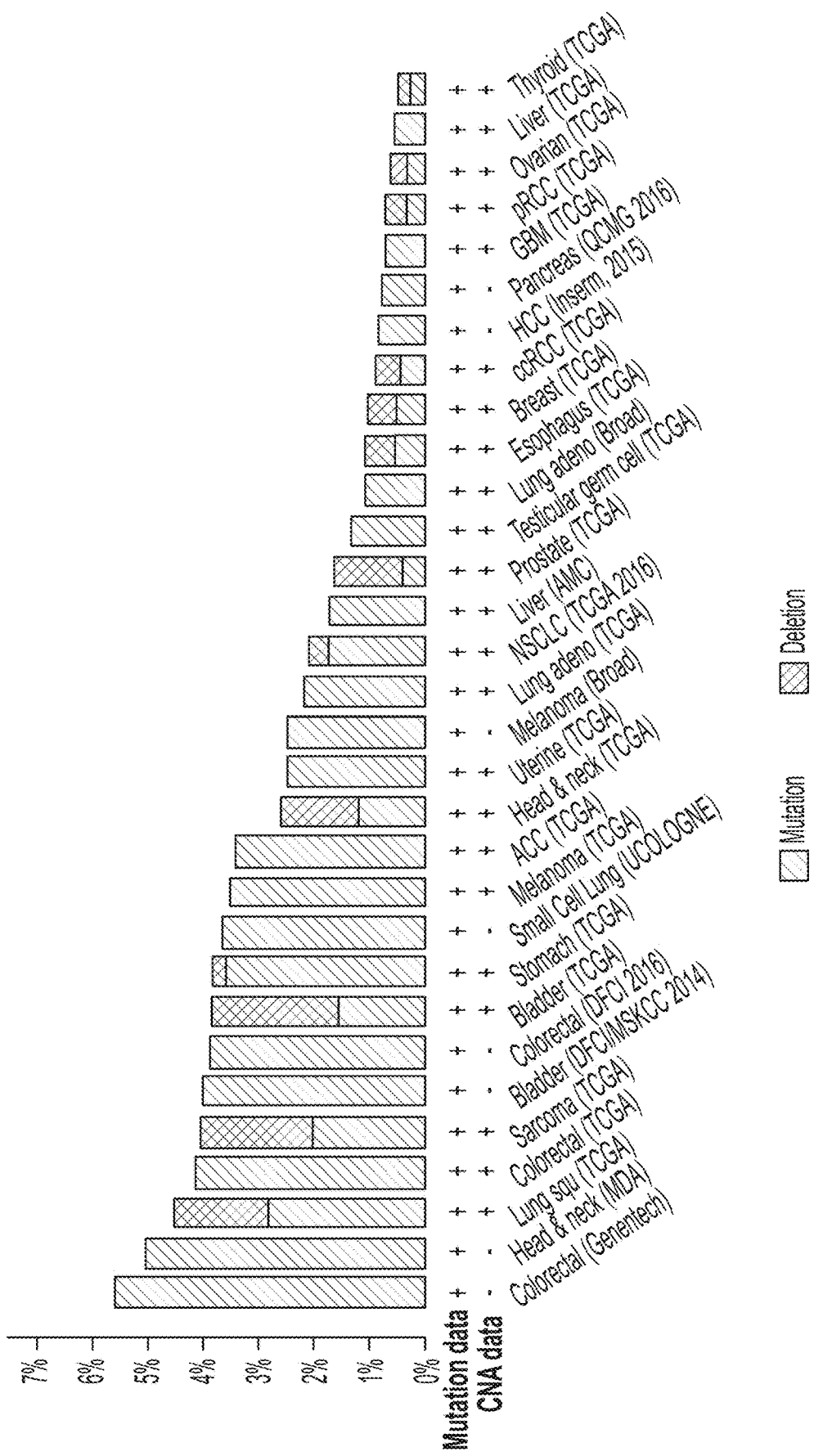
FIG. 11A-11C. Lentiviral-mediated delivery of mutagenized constructs of SMARCAL1 in two ALT-positive lines lacking SMARCAL1 expression.
Figure 11B:
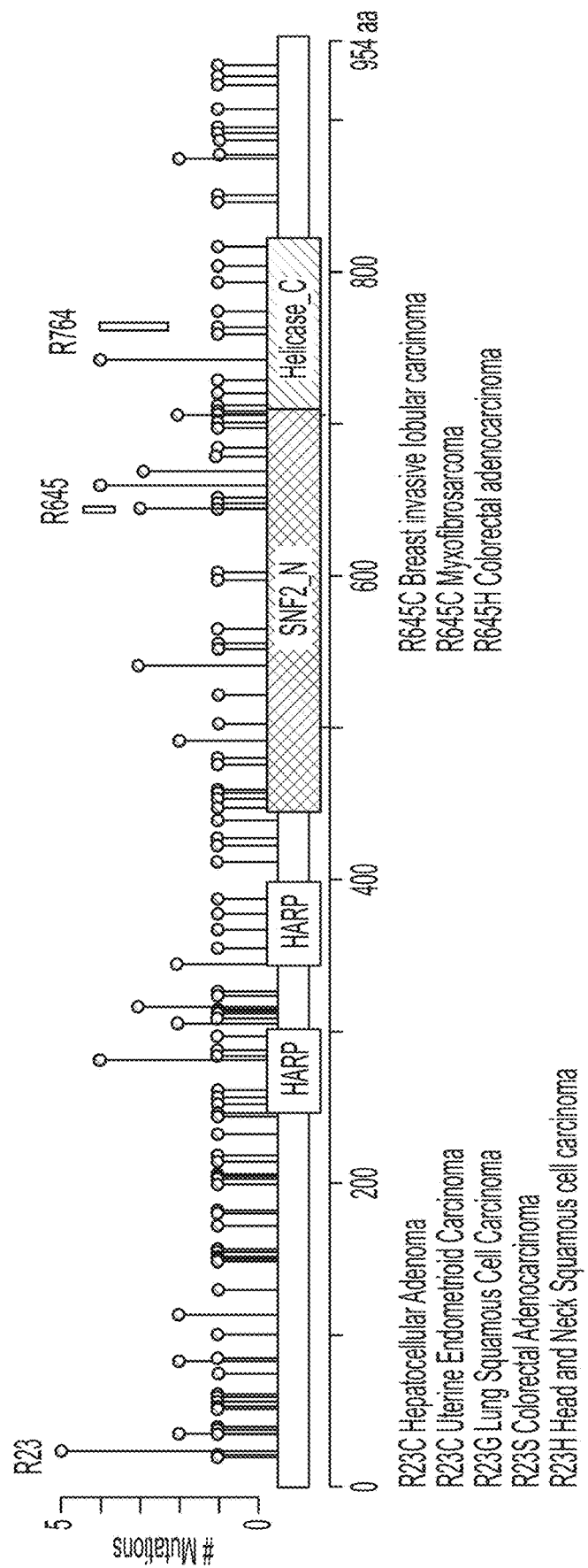
Figure 11C:
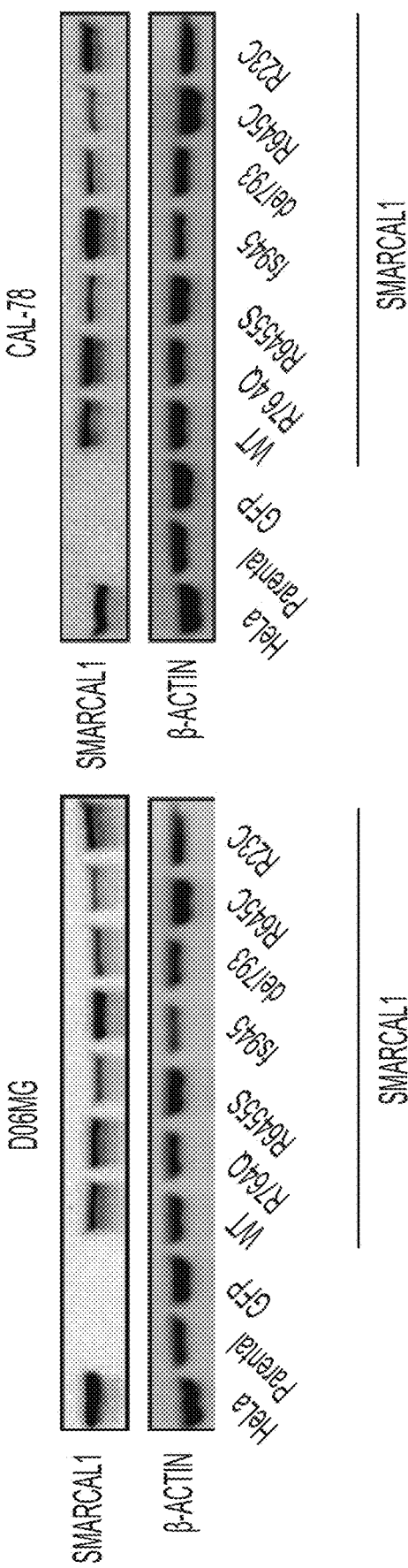

Lentiviral expression of SMARCAL1 cDNA was done using a constitutive (pLX304) expression vector. pLX304-SMARCAL1 was provided by DNASU (HsCD00445611) and the control pLX304-GFP was a generous gift from Dr. So Young Kim (Duke Functional Genomics Core). Mutagenesis constructs of pLX304-SMARCAL1 (R23C, R645C, R645S, del793, fs945, and R764Q) were generated per the manufacturer's directions using the QuikChange II Site-Directed Mutagenesis Kit (Agilent). Endotoxin-free plasmids were purified using the ZymoPURE plasmid midiprep kit (Zymo Research) and validated by sequencing and analytical digest. Lentivirus was generated using standard techniques, with the SMARCAL1 cDNA vector, psPAX2 packaging and pMD2.G envelope plasmids in HEK293 and the virus titers were determined using the Resazurin Cell Viability Assay (Duke Functional Genomics Core Facility). Prior to transduction, cell media were replaced with fresh media containing 8 µg/mL polybrene and cells were then spin-infected with lentivirus at a multiplicity of infection of 1 (2250 rpm, 30 min at 37° C.). After 48 h, selection was initiated with blasticidin (pLX304). Transgene expression was confirmed by western blot (FIG. 11).

Immunoblotting

Cells were lysed in protein-denaturing lysis buffer and protein was quantified using the BCA Protein Assay Kit (Pierce). Equal amounts of protein were loaded on SDS-polyacrylamide gels (3-8% Tris-Acetate for blots probing for ATRX, 4-12% bis-tris for all others), transferred to membranes, blocked, and blotted with antibodies. Antibodies used included anti-SMARCAL1 (Cell Signaling Technologies), anti-ATRX (Cell Signaling Technologies), anti-β-Actin (Cell Signaling Technologies), and anti-GAPDH (Santa Cruz Biotechnology) for equal loading control. Original blots are provided in FIGS. 15-16.

Immunohistochemistry

Immunolabeling for the ATRX protein was performed on FFPE sections as previously described[67]. Briefly, heat-induced antigen retrieval was performed using citrate buffer (pH 6.0, Vector Laboratories). Endogenous peroxidase was blocked with a dual endogenous enzyme-blocking reagent (Dako). Slides were incubated with the primary antibody rabbit anti-human ATRX (Sigma HPA001906, 1:400 dilution) for 1 h at room temperature and with horseradish peroxidase-labeled secondary antibody (Leica Microsystems), followed by detection with 3,3'-Diaminobenzidine (Sigma-Aldrich) and counterstaining with hematoxylin, rehydration, and mounting. IHC for several cases in the validation cohort was also immunolabeled by HistoWiz Inc. (histowiz.com) using a Bond Rx autostainer (Leica Biosystems) with heat-mediated antigen retrieval using standard protocols. Slides were incubated with the aforementioned ATRX antibody (1:500), and Bond Polymer Refine Detection (Leica Biosystems) was used according to the manufacturer's protocol. Sections were counterstained with hematoxylin, dehydrated, and film coverslipped using a TissueTek-Prisma and Coverslipper (Sakura). Nuclear staining of ATRX was evaluated by a neuropathologist.

C-Circle Assay

C-circle assay was performed as previously described by dot blot[20,68]. Then, C-circles were amplified from 50 ng of DNA by rolling circle amplification for 8 h at 30° C. with φ29 polymerase (NEB), 4 mM dithiothreitol, 1×φ29 buffer, 0.2 mg/mL bovine serum albumin (BSA), 0.1% Tween, and 25 mM of dATP, dGTP, dCTP, and dTTP. C-circles were then blotted onto Hybond-N+ (GE Amersham) nylon membranes with the BioDot (Bio-Rad) and ultraviolet light crosslinked twice at 1200J (Stratagene). Prehybridization and hybridization were done using the TeloTAGGG telomere length assay (Sigma-Aldrich/Roche) and detected using a DIG-labeled telomere probe. DNA from ALT-positive (U2-OS) and -negative (HeLa) cell lines were used as controls.

Combined Immunofluorescence FISH

Cells were grown on coverslips or μ-slides (Ibidi) to subconfluence and immunofluorescence FISH (IF-FISH) was performed as previously described[69], using the primary antibodies against SMARCAL1 (mouse monoclonal, sc-376377, Santa Cruz Biotechnology, 1:100) and PML (rabbit polyclonal, ab53773, Abcam, 1:200) in blocking solution (1 mg/mL BSA, 3% goat serum, 0.1% Triton X-100, 1 mM EDTA) overnight at 4° C. Briefly, cells were fixed with 2% formaldehyde. After washing with phosphate-buffered saline (PBS), slides were incubated with goat secondary antibodies against rabbit or mouse IgG, then conjugated with Alexa Fluor 488 or 594 (ThermoFisher, 1:100) in blocking solution. After washing with PBS, cells were fixed again with 2% formaldehyde for 10 min, and washed once again with PBS. Cells underwent a dehydration series (70%, 95%, 100% ethanol), and then incubated with PNA probes (each 1:1000) TelC-Cy3 and Cent-FAM (PNA Bio) in hybridizing solution, denatured at 70° C. for 5 min on a ThermoBrite system, then incubated in the dark for 2 h at room temperature. Slides were then washed with 70% formamide 10 mM Tris-HCl, PBS, and then stained with 4 §-diamidino-2-phenylindole (DAPI) and sealed.

Telomere FISH

Deparaffinized slides were hydrated and steamed for 25 min in citrate buffer (Vector Labs), dehydrated, and hybridized with TelC-Cy3 and Cent-FAM (PNA Bio) or CENP-B-AlexaFluor488 in hybridization solution. The remaining steps were done as in combined IF-FISH (above). ALT-positive tumors in FFPE tissue displayed dramatic cell-to-cell telomere length heterogeneity as well as the presence of ultrabright nuclear foci of telomere FISH signals. Cases were visually assessed and classified as ALT positive if: (i) they displayed ultrabright nuclear foci (telomere FISH signal, 10-fold greater than the signal for individual non-neoplastic cells); and (ii) ≥1% of tumor cells displayed ALT-associated telomeric foci. Areas of necrosis were excluded from analysis. For analysis of ALT status in mutagenesis SMARCAL1 rescue experiments and assessment of ALT status in CRISPR/Cas9 SMARCAL1 knockout experiments, cells were made into formalin-fixed paraffin blocks for easier telomere FISH assessment and quantitative measurement of differences. Briefly, cells were trypsinized, centrifuged onto 2% agarose, fixed in 10% formalin several times to form a fixed cell line plug, then processed, paraffin embedded, and sectioned. For quantitative measurements of differences in ultrabright telomeric foci, telomere FISH-stained slides were scanned at 10× and 20 random fields were selected for assessing the percentage of cells showing ultrabright telomeric foci (~200 cells counted per field).

1p/19q Co-Deletion Testing

1p/19q co-deletion was assessed by either microsatellite-based loss of heterozygosity (LOH) analysis[70] (on DNA extracted from tumor samples and matched germline blood DNA) or by FISH (ARUP labs) on FFPE slides.

Sanger Sequencing

PCR purification and sequencing reactions were performed by Eton Biosciences or Genewiz using an ABI 3730xl DNA sequencer. PCR reaction conditions and primers are listed in Supplementary Data 14☐15 available on-line at Nature Communications as the supplementary data associated with the article at volume 9, page 2087.

Colony-Forming Assay

The CAL78-GFP and CAL78-SMARCAL1 cell lines were seeded in triplicate at 2000 cells per well. D06MG-GFP and D06MG-SMARCAL1 cell lines were seeded in triplicate at 1000 cells per well. Cells were fixed with ice-cold methanol and stained with 0.05% crystal violet solution after 15☐30 days of incubation. Colony area was quantified using ImageJ and the ColonyArea plugin[71].

Statistical Analysis

GraphPad Prism 7 and R were used for all statistical analyses (t-test, Kruskal Wallis test, Fisher's exact test, and Kaplan☐Meier curves). Kaplan-Meier analysis was performed for patients with available survival data diagnosed after the year 2000.

Data Availability

Whole exome sequencing and whole genome sequencing data have been deposited on the Sequencing Read Archive (SRA), accession code: SRP136708.

Example 2

The Genetic Landscape of $TERTp^{WT}$-$IDH^{WT}$ GBM

Figure 6:
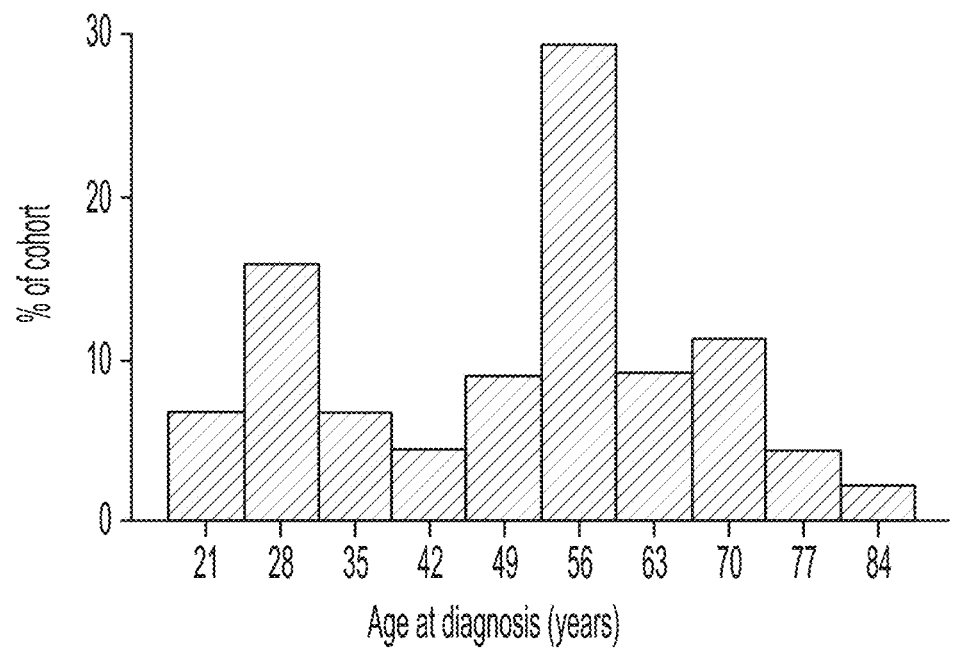
FIG. 6. Age distribution of TERTp$^{WT}$-IDH$^{WT}$ glioblastoma patients. The distribution of patient age for the TERTp$^{WT}$-IDH$^{WT}$ glioma cohort is shown as a percentage of the entire group. Two modes are identified in the cohort, one at 28 years, the other at 56 years of age (N=44).

We identified a cohort of patients with tumors that were $TERTp^{WT}$-$IDH^{WT}$ by screening 260 GBMs for mutations in the TERT promoter and IDH1/2. Forty-four $TERTp^{WT}$-$IDH^{WT}$ cases were identified, which comprised 16.9% of the total GBM cohort[4]. The $TERTp^{WT}$-$IDH^{WT}$ GBMs with available 1p/19q status available did not display 1p/19q co-deletion, consistent with previous reports that have labeled these tumors ☐triple-negative☐due to the observation that they lack all three common diffuse glioma biomarkers ($TERTp^{WT}$-$IDH^{WT}$-$1p/19q^{WT}$)[8]. The age distribution of the $TERTp^{WT}$-$IDH^{WT}$ GBM cohort was bimodal, with one mode at 28 years and the other at 56 years (range: 18 to 82 years). Approximately 30% (13/44) of $TERTp^{WT}$-$IDH^{WT}$ GBMs were younger than 40 years old (FIG. 1, FIG. 6, Supplementary Data 1-2 available on-line at Nature Communications as the supplementary data associated with the article at volume 9, page 2087). We performed WES on cases for which DNA from untreated tumor tissue and matched peripheral blood were available (Discovery cohort, N=25). The average sequencing coverage was 140-fold (range: 70 to 265) and 92% of bases had at least 10 high-quality reads (range: 87 to 94%). We identified 1449 total somatic, non-synonymous mutations in the exomes of the $TERTp^{WT}$-$IDH^{WT}$ GBMs, with each having an average of 58 mutations per tumor (range: 6 to 431, FIG. 1), resulting in an average mutation rate of approximately 1.74 coding mutations per Mb, similar to rates observed in GBMs from previous studies (1.5 mutations/Mb)[7].

The mutational landscape of $TERTp^{WT}$-$IDH^{WT}$ GBM is shown in FIG. 1. Recurrently mutated genes in $TERTp^{WT}$-$IDH^{WT}$ GBM occurred in pathways including the RTK/RAS/PI3K (88%), P53 (40%), and RB (24%) pathways (FIG. 1, Supplementary Data 3-5 available on-line at Nature Communications as the supplementary data associated with the article at volume 9, page 2087). Additional genes harboring copy number variations included PDGFRA (8%), MDM2 and MDM4 (12%), CDKN2B (12%), and CDK4 (FIG. 1, Supplementary Data 5 available on-line at Nature Communications as the supplementary data associated with the article at volume 9, page 2087). At least one recurrently mutated gene (n≥2) was identifiable in 92% of the $TERTp^{WT}$-$IDH^{WT}$ GBMs.

IntOGen analysis[21,22] identified several known glioma-associated driver alterations (P<0.05, n≥2), including PTEN (32%), NF1 (24%), EGFR (28%), TP53 (24%), ATRX (20%), and BRAF (20%), as well as two novel candidate drivers, SMARCAL1 (16%) and PPM1D (8%) (Supplementary Data 6 available on-line at Nature Communications as the supplementary data associated with the article at volume 9, page 2087), both of which have not previously been implicated as drivers in adult supratentorial GBM. All mutations identified in the serine/threonine protein kinase BRAF were V600E, the clinically actionable hotspot mutation that causes increased kinase activity and RAS pathway activation. BRAF mutations occurred significantly more often than previous studies (20% vs. 1.7% of GBM[23], P=0.0007, two-sided Fisher's exact test). Most of these alterations (4/5, 80%) were present in adult patients ≤30 years old (P=0.0019, two-sided Fisher's exact test). The PPM1D mutations identified were located in the C-terminal regulatory domain (exon 6), leading to a truncated protein with an intact phosphatase domain, similar to PPM1D mutations described in gliomas of the brainstem[11].

Example 3

SMARCAL1-mutant GBMs exhibit hallmarks of ALT
The mutations identified in the novel candidate driver SMARCAL1 were primarily nonsense or frameshift with mutant allele fractions greater than 50% (average: 69%; range: 59☐83%), indicating likely loss of heterozygosity and a loss-of-function mutational pattern. SMARCAL1 encodes an adenosine triphosphate (ATP)-dependent annealing helicase that has roles in catalyzing the rewinding of RPA-bound DNA at stalled replication forks[24,25], and was recently shown to be involved in resolving telomere-associated replication stress[26,27]. SMARCAL1 has similarities with ATRX, which is also a member of the SWI/SNF family of chromatin remodelers and has both ATP-binding and C-terminal helicase domains[28]. Additionally, ATRX harbors recurrent loss-of-function mutations that result in loss of nuclear expression in ALT-positive gliomas[10,13,17].

Given these similarities to ATRX, we sought to determine if SMARCAL1-mutant tumors exhibit markers of ALT, including C-circles and ultrabright telomeric foci (telomere fluorescent in situ hybridization (FISH))[20,29]. We expanded the cohort of TERTp$^{WT}$-IDH$^{WT}$ GBMs (N=39) and sequenced SMARCAL1, identifying mutations in 21% (8/39) of tumors, with the majority (75%, 6/8) of these alterations being frameshift, nonsense, or splice site mutations (FIG. 2a). All SMARCAL1-mutant GBMs exhibited both ultrabright telomeric foci and C-circles, suggesting a novel link between somatic SMARCAL1 loss-of-function mutations in cancer and the ALT mechanism of telomere maintenance. Additionally, by assaying ATRX expression by immunohistochemistry (IHC), we found that loss of nuclear ATRX was observed in 22% (8/37) of TERTp$^{WT}$-IDH$^{WT}$ GBMs. Overall, 36% (14/39) of TERTp$^{WT}$-IDH$^{WT}$ GBMs exhibited both ultrabright telomeric foci and C-circles, which are hallmarks consistent with the ALT phenotype. Of these ALT-positive tumors, 46.7% (7/15) showed loss of nuclear ATRX expression, while the other 53.3% (8/15) harbored SMARCAL1 mutations, exhibiting a mutually exclusive pattern (P=0.01, Fisher's exact test, two-tailed, odds ratio=0.024, FIG. 2a). Finally, based on exome sequencing results, 80% (8/10) of the ALT-positive TERTp$^{WT}$-IDH$^{WT}$ GBMs also harbored alterations in NF1 or BRAF, indicating a potential Example 4

Identification of TERT Rearrangements in TERTp$^{WT}$-IDH$^{WT}$ GBM
Based on the measurement of markers of ALT, 61.5% (24/39) of TERTp$^{WT}$-IDH$^{WT}$ GBMs did not exhibit ultrabright foci or C-circle accumulation (ALT negative), suggesting that these cases may utilize a telomerase-dependent mechanism of telomere maintenance, independent of TERTp mutation (FIG. 2a). We sought to identify genetic alterations impacting telomerase activity that would not be detectable by exome sequencing.

Figure 7:
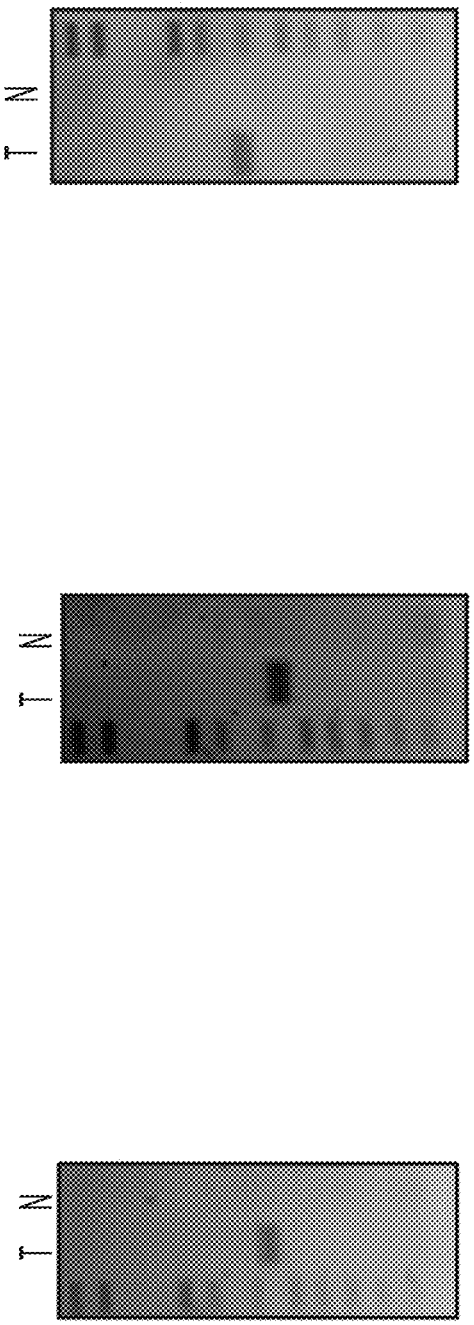
FIG. 7. Breakpoint-spanning PCR and sequencing confirms TERT rearrangements. Whole genome sequencing data was analyzed for structural variants. Rearrangements upstream of TERT were identified by DELLY, which also identified the corresponding breakpoint. Primers were designed spanning the breakpoints and PCR was performed to confirm the somatic nature of these breakpoints (T: Tumor and N: Normal gDNA from blood for the same patient).
Figure 7:
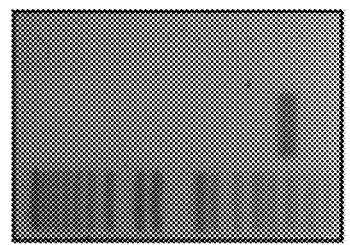
Figure 8A:
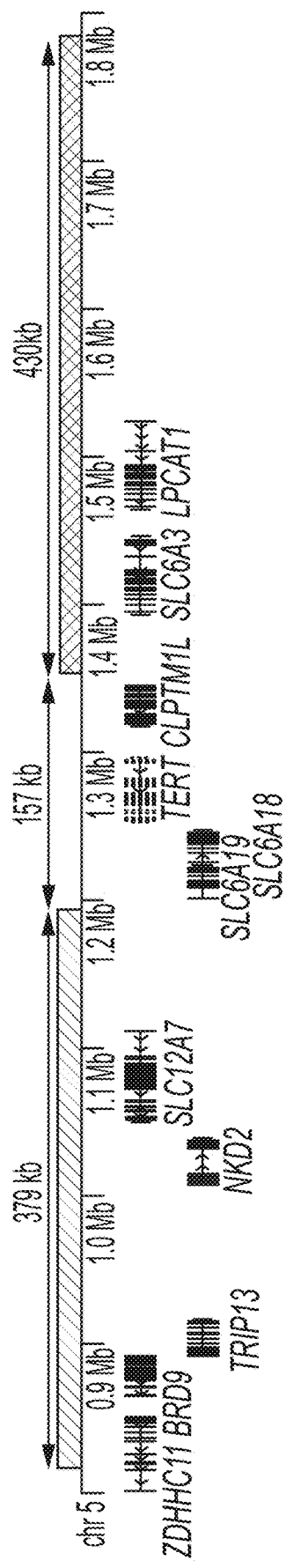

We performed WGS on ALT-negative TERTp$^{WT}$-IDH$^{WT}$ GBMs (N=8) and their paired matched normal genomic DNA (Supplementary Data 7☐10 available on-line at Nature Communications as the supplementary data associated with the article at volume 9, page 2087). Structural variant analysis[30] identified recurrent rearrangements upstream of TERT in 75% (6/8) of the ALT-negative TERTp$^{WT}$-IDH$^{WT}$ GBMs sequenced (FIG. 2b, c). Half of these rearrangements were translocations to other chromosomes, while the remaining were intrachromosomal inversions. Breakpoints were validated as tumor specific by junction-spanning PCR in five of six cases (FIG. 7). To detect TERT structural variants in the entire TERTp$^{WT}$-IDH$^{WT}$ GBM cohort, we used break-apart FISH with probes spanning TERT (FIG. 2D, FIG. 8A-8B). In total, we found 50% (19/38) of the TERTp$^{WT}$-IDH$^{WT}$ GBMs harbored TERT structural rearrangements. TERT-rearranged GBMs exhibited mutual exclusivity with the ALT-positive TERTp$^{WT}$-IDH$^{WT}$ GBMs (P=0.0019, Fisher's exact test, two-tailed, odds ratio=0.069). Analysis of TERT messenger RNA (mRNA) expression revealed that TERT-rearranged GBMs express significantly higher levels of TERT compared to the ALT-positive (ATRX and SMARCAL1-mutant) TERTp$^{WT}$-IDH$^{WT}$ GBMs (P=0.016, Kruskal ☐Wallis test using Dunn's test post hoc, FIG. 2e). This is a similar pattern to that observed between the other two major GBM subtypes, where telomerase-positive, IDH$^{WT}$-TERTp$^{MUT}$ GBMs exhibit significantly higher TERT mRNA expression (P=0.0036, Kruskal ☐Wallis test using Dunn's test post hoc) relative to the IDH$^{MUT}$-TERTp$^{WT}$ GBMs, which are ATRX mutated and exhibit ALT[10]. There were no significant differences in TERT expression between the TERT$^{SV}$ and TERTp mutant subgroups (or between the IDH-mutant and IDH$^{WT}$-ALT subgroups). Of the seven remaining ALT-negative tumors that lacked TERT rearrangement, one tumor harbored amplification of MYC, a known transcriptional activator of TERT[31], and this tumor displayed elevated TERT expression (FIG. 2e, arrow).

Example 5

Figure 3:
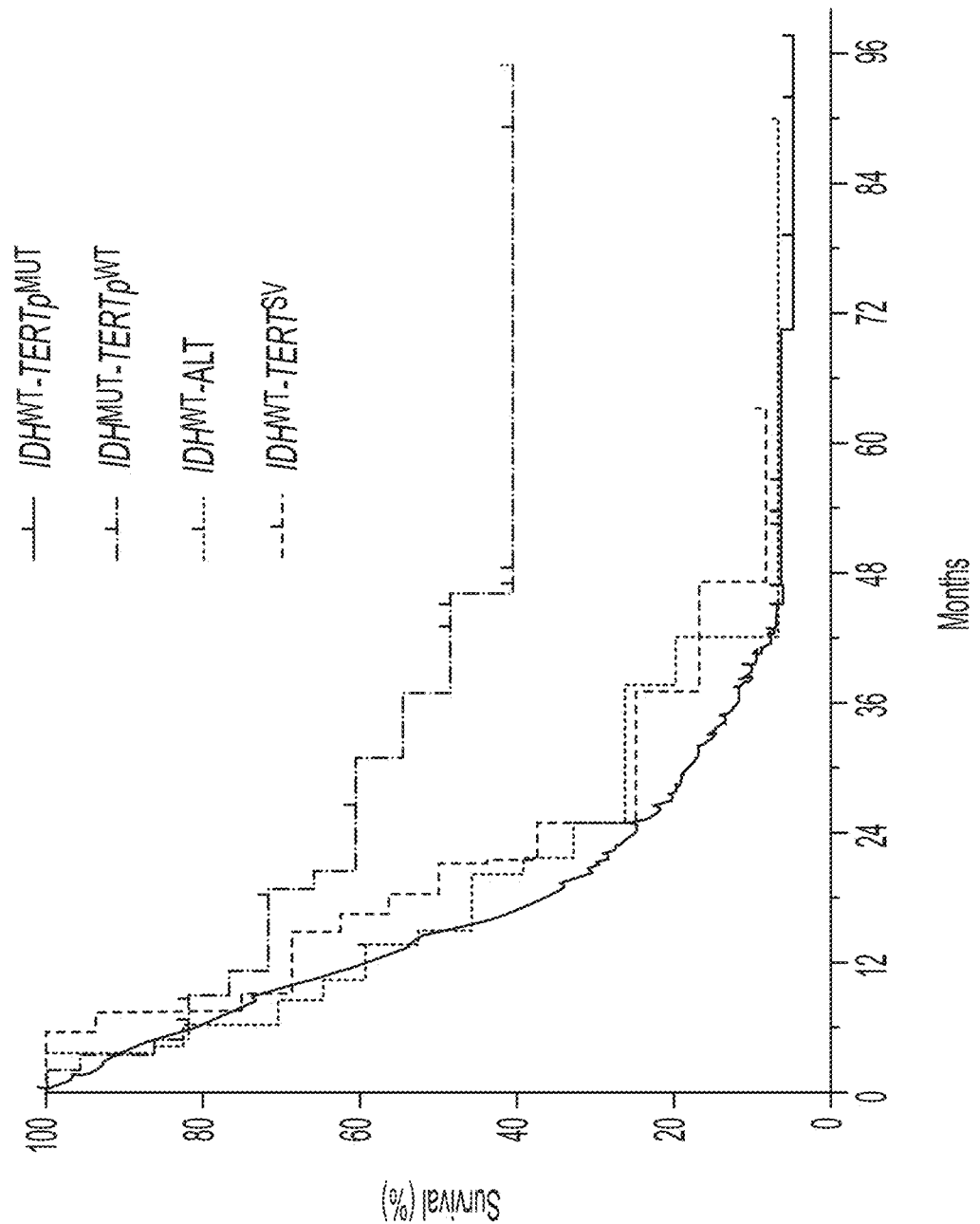
FIG. 3. New genetic subgroups of GBM display distinct survival patterns. Kaplan-Meier analysis of GBMs grouped by recurrent alterations identified in this study, including SMARCAL1/ATRX mutation (IDH$^{WT}$-ALT) and TERT rearrangement (IDH$^{WT}$-TERT$^{SV}$). The survival of these new groups are compared to established subgroups of GBM including TERT promoter-mutant (IDH$^{WT}$-TE New genetic subgroups of GBM display distinct survival patterns. Kaplan-Meier analysis of GBMs grouped by recurrent alterations identified in this study, including SMARCAL1/ATRX mutation (IDHWT-ALT) and TERT rearrangement (IDHW$^T$-TERT$^{SV}$). The survival of these new groups are compared to established subgroups of GBM including TERT promoter-mutant (IDH$^{WT}$-TERTp$^{MUT}$, N=223) and IDH-mutant GBMs (IDHM$^{UT}$-TERT$^{WT}$, N=23), with median overall survivals of 14.74 and 37.08 months, respectively. Patients in the IDH$^{WT}$-other GBM subgroup (N=7) were excluded due to the limited number of patients. The median OS for the IDH$^{WT}$-ALT subgroup (N=17) was 14.9 months, while the IDH$^{WT}$-TERT$^{SV}$ subgroup (N=16) had an OS of 19.7 months. Compared to the IDH$^{MUT}$-TERT$^{WT}$ GBMs, the IDH$^{WT}$-TERTp$^{MUT}$ (P=0.0003, HR=2.867, 95% CI: 1.929 to 4.262), IDH$^{WT}$-ALT (P=0.0281, HR=2.302, 95% CI: 1.039 to 5.1), and IDHW$^T$-TERT$^{SV}$ GBMs (P=0.0794, HR=1.982, 95% CI: 0.8878 to 4.427) have poorer survival. Comparison of survival curves done by log-rank (Mantel ☐Cox) tes-tRTp$^{MUTi}$ N=223) and IDH-mutant GBMs (IDH$^{MUT}$-TERT$^{WT}$, N=23), with median overall survivals of 14.74 and 37.08 months, respectively. Patients in the IDH$^{WT}$-other GBM subgroup (N=7) were excluded due to the limited number of patients. The median OS for the IDH$^{WT}$-ALT subgroup (N=17) was 14.9 months, while the IDH$^{WT}$-TERT$^{SV}$ subgroup (N=16) had an OS of 19.7 months. Compared to the IDH$^{MUT}$-TERT$^{WT}$ GBMs, the IDH$^{WT}$-TERTp$^{MUT}$ (P=0.0003, HR=2.867, 95% CI: 1.929 to 4.262), IDH$^{WT}$-ALT (P=0.0281, HR=2.302, 95% CI: 1.039 to 5.1), and IDH$^{WT}$-TERT$^{SV}$ GBMs (P=0.0794, HR=1.982, 95% CI: 0.8878 to 4.427) have poorer survival. Comparison of survival curves done by log-rank (Mantel ☐Cox) test.

Telomere-Related Alterations Define New Subgroups of GBM
Using whole exome and genome sequencing, we identified frequent telomere maintenance-related alterations that define new genetic subgroups of GBM. The IDH$^{WT}$-ALT GBM subgroup, which harbors ATRX and SMARCAL1 mutations, accounts for 38.5% of TERTp$^{WT}$-IDH$^{WT}$ GBMs and exhibits characteristics consistent with ALT. The IDH$^{WT}$-TERT$^{SV}$ GBM subgroup harbors TERT structural variants and exhibits increased TERT expression. Together, these two subgroups accounted for 82% (32/39) of the TERTp$^{WT}$-IDH$^{WT}$ GBMs, and exhibited mutual exclusivity (P=0.0019, Fisher's exact test, two-tailed, odds ratio=0.069). Kaplan☐Meier survival analyses revealed that the IDH$^{WT}$-ALT (OS: 14.9 months), and IDH$^{WT}$-TERT$^{SV}$ (OS: 19.7 months) subgroups exhibit poor survival, similar to the IDH$^{WT}$-TERTp$^{MUT}$ subgroup (OS: 14.74 months). All of these IDH$^{WT}$ subgroups displayed shorter OS relative to the IDH$^{MUT}$-TERTp$^{WT}$ subgroup (OS: 37.08 months, FIG. 3).

Example 6

SMARCAL1 Mutations Contribute to ALT Telomere Maintenance

Figure 9A:
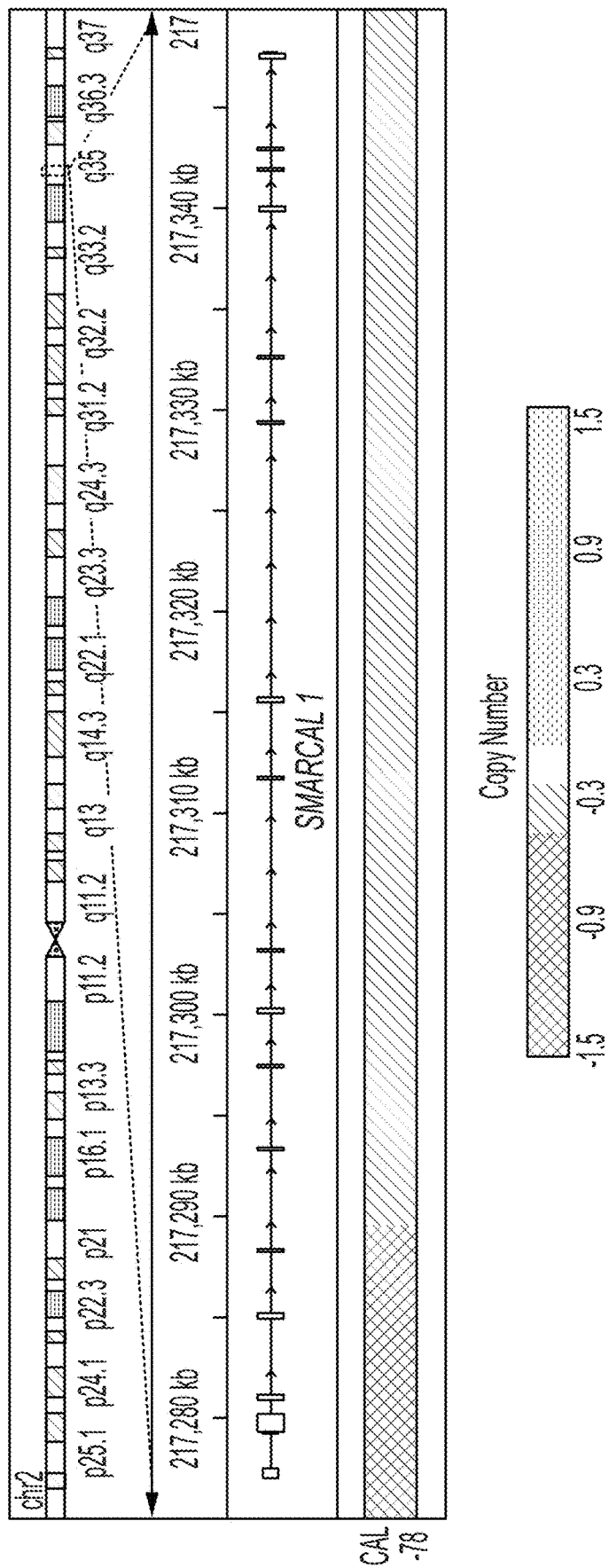
FIG. 9A-9D. CAL-78 and D06MG are cell lines with mutations in SMARCAL1.
Figure 9B:
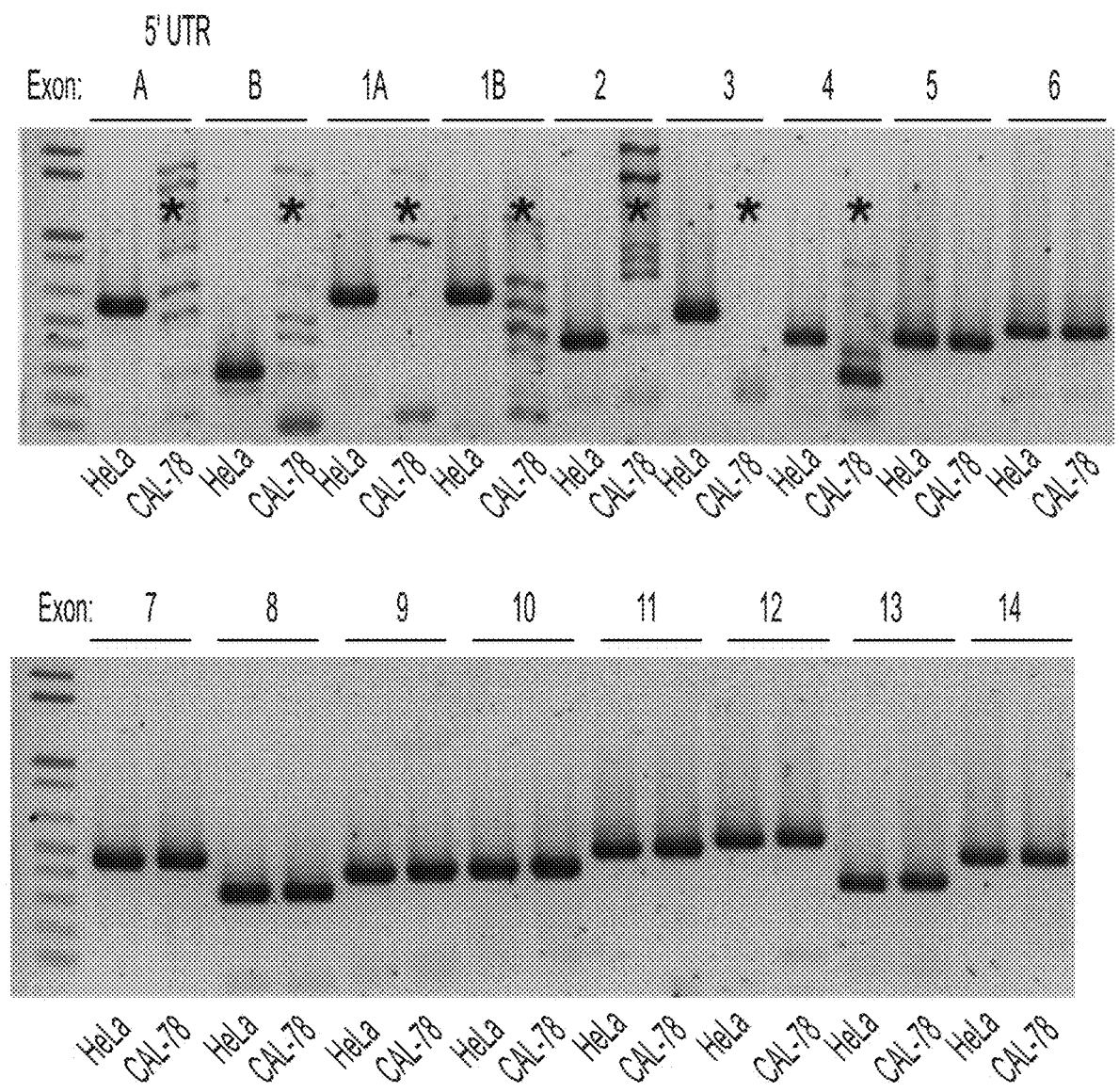
Figure 9C:
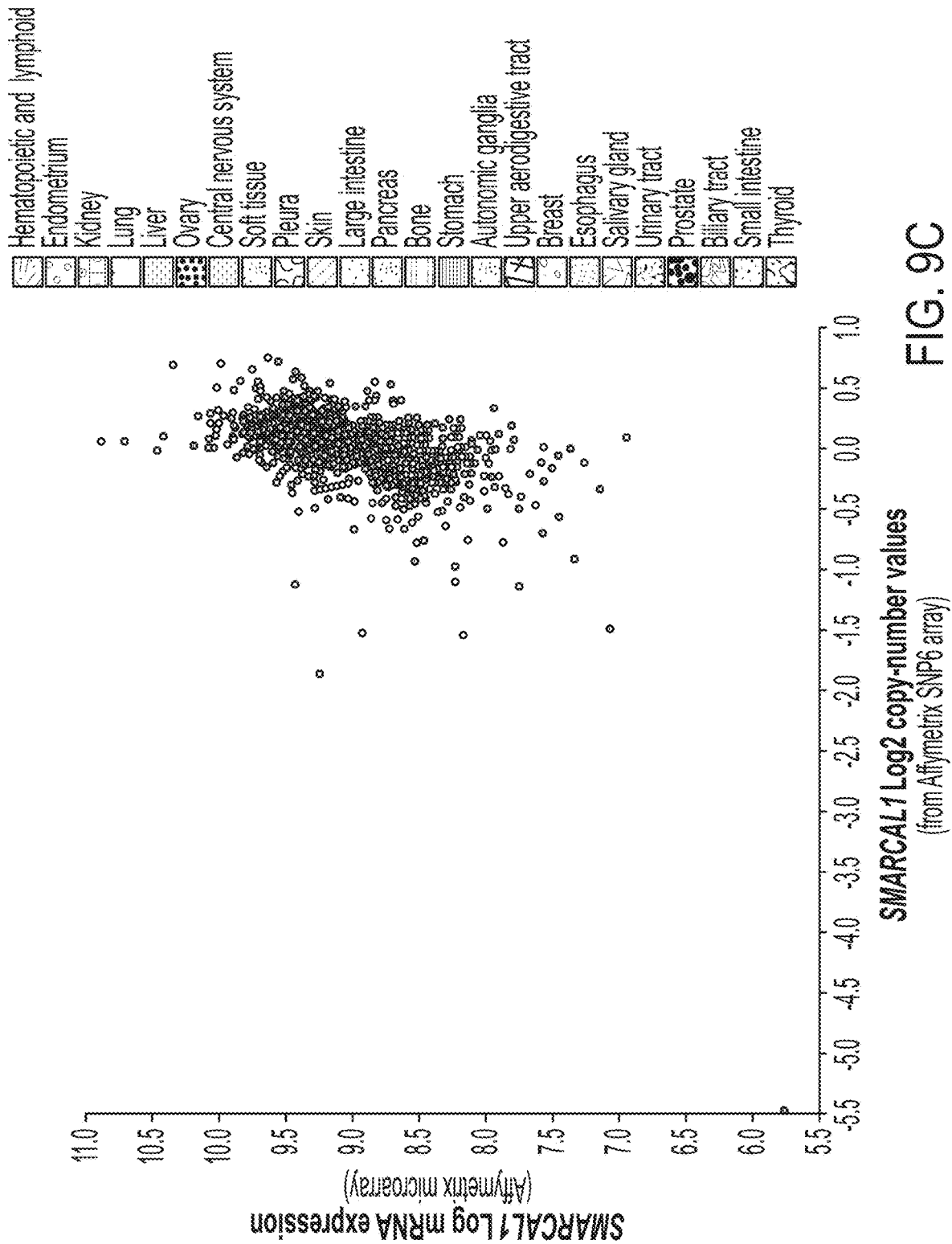
Figure 9D:
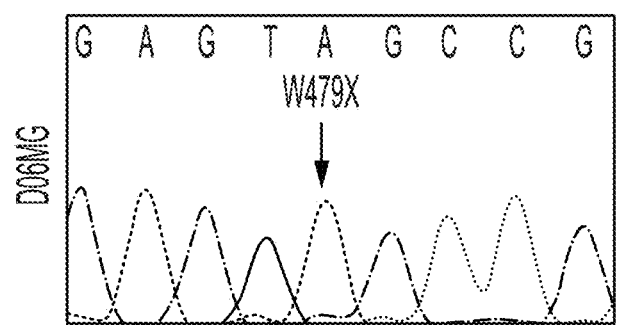
Figure 10A:
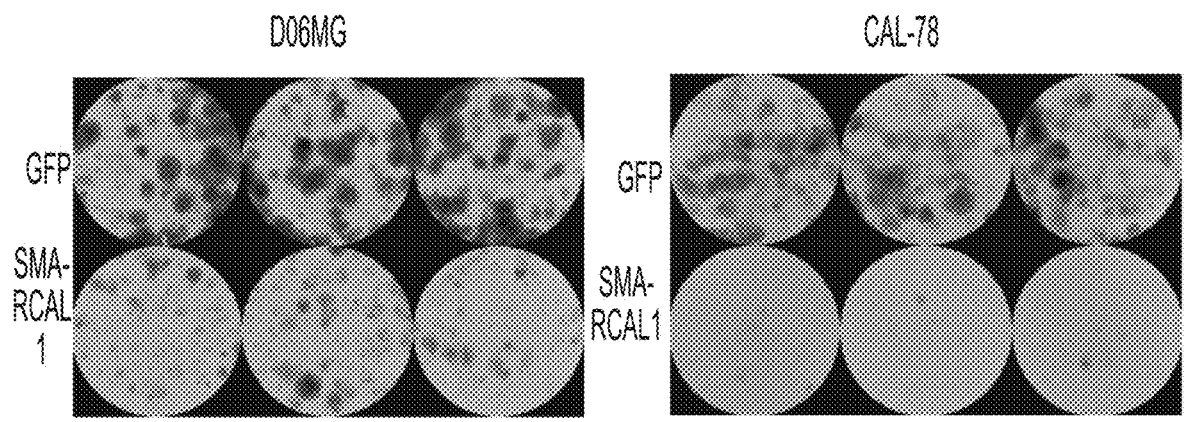
FIG. 10A-10C. Rescue of SMARCAL1 expression in CAL-78 and D06MG inhibits colony formation. We rescued expression of wildtype SMARCAL1 in FIG. 10A: D06MG and FIG. 10B, CAL-78. The top images are black and white images of the colony formation result after crystal violet staining. The bottom image is after thresholding to show differences in area and intensity.
Figure 10B:
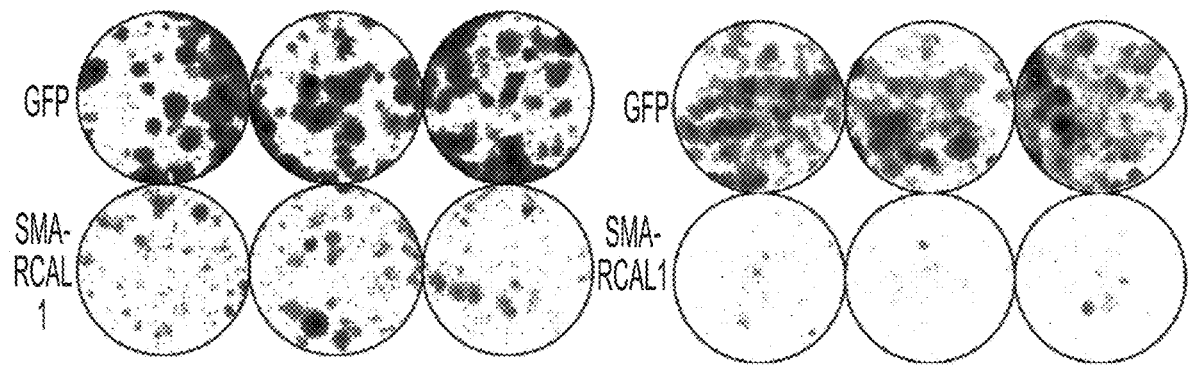
Figure 10C:
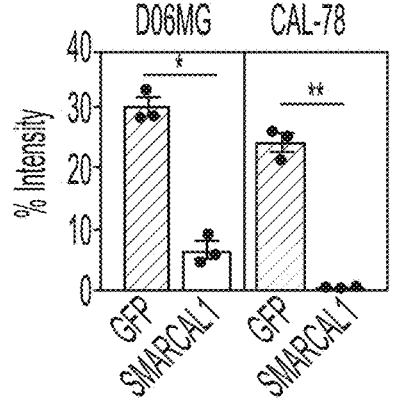

The exome sequencing and ALT results indicate that there is a strong correlation between recurrent somatic inactivating mutation of SMARCAL1 and ALT telomere maintenance in a subset of GBMs, similar to the previously established roles of ATRX and DAXX mutations[13] (FIG. 4a). To further explore the functional connection between somatic SMARCAL1 mutations and ALT, we identified two cancer cell lines harboring mutations in SMARCAL1, D06MG, and CAL-78. D06MG is a primary GBM cell line harboring a nonsense, homozygous SMARCAL1 mutation (W479X, FIG. 9D), derived from the tumor of patient DUMC-06. CAL-78 is a chondrosarcoma cell line with homozygous deletion of the first four exons of SMARCAL1, resulting in loss of expression (FIGS. 9A-9C)[32]. Both SMARCAL1-mutant cell lines exhibited total loss of SMARCAL1 protein expression by western blot, with intact expression of ATRX and DAXX (FIG. 4c) and hallmarks consistent with ALT, including ALT-associated promyelocytic leukemia (PML) bodies (APBs), DNA C-circles, and ultrabright telomere DNA foci[13,17,33] (FIG. 4b). Restoration of SMARCAL1 expression in these cell lines significantly reduced colony forming ability, supporting the role of SMARCAL1 as a tumor suppressor (FIG. 4D, FIGS. 10A-10C).

We then investigated the extent to which expression of wildtype (WT) SMARCAL1 or cancer-associated SMARCAL1 variants modulate ALT hallmarks in cell lines with native SMARCAL1 mutations. We found that SMARCAL1 WT expression markedly suppressed ultrabright telomeric foci in both CAL-78 and D06MG. (FIG. 4e). Next, we sought to investigate the effects of somatic SMARCAL1 variants on C-circle abundance. Cancer-associated mutations tested from our GBM cohort included SMARCAL1 Arg645Ser (R645S), Phe793del (del793), and Gly945fs*1 (945 fs). In addition, we examined mutation patterns in pan-cancer TCGA (The Cancer Genome Atlas) data on cBioportal[34] and found that SMARCAL1 mutations and homozygous deletions are present at low frequency in several other cancer types (FIG. 11A). We tested two SMARCAL1 recurrent variants, R23C and R645C, that were identified from these sequencing studies. R23 (n=5 mutations) is located in the RPA-binding domain, while R645 (n=3 mutations) is located in the SNF2 helicase domain, similar to the R645S variant identified in our cohort (FIG. 11B).

SMARCAL1 WT expression in both CAL-78 and D06MG significantly suppressed C-circle abundance relative to the control condition. In contrast, expression of SMARCAL1 R764Q, a well-studied helicase loss-of-function mutation found in a patient with Schimke immuneosseous dysplasia (SIOD)[35], failed to fully suppress C-circles in CAL-78 and D06MG, demonstrating that SMARCAL1 helicase activity is critical for suppression of these ALT features. Rescue with SMARCAL1 R645S, R645C, and del793 failed to fully suppress C-circles in both cell lines, similar to R764Q. However, overexpression of the SMARCAL1 R23C and fs945 constructs resulted in a similar suppression of C-circle levels to that of the wildtype rescue (FIG. 4g). Notably, the GBM case with SMARCAL1 fs945 mutation from our study exhibited concurrent loss of ATRX expression by IHC, indicating that perhaps ATRX loss was the primary genetic lesion associated with ALT in this case.

Figure 5:
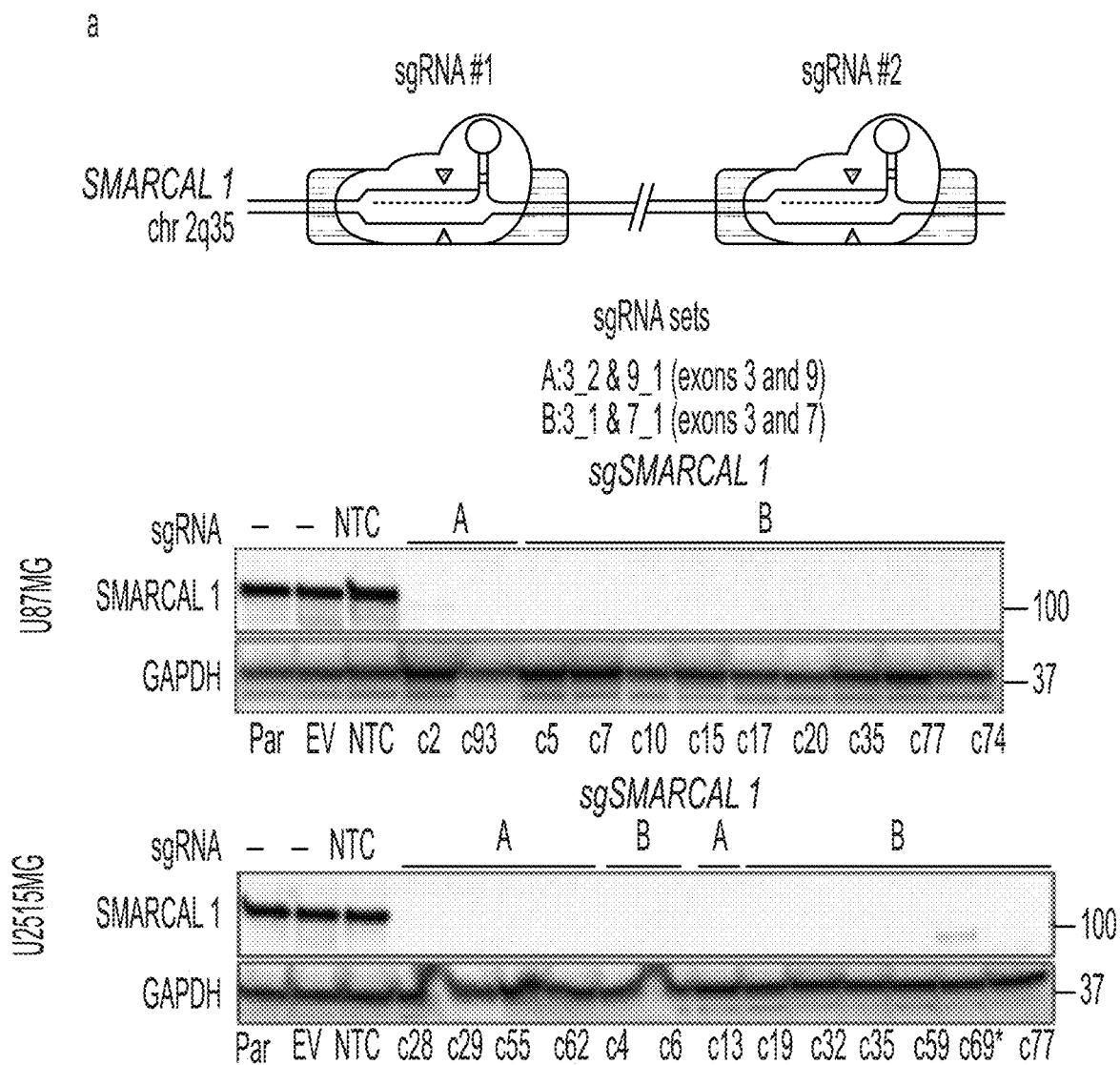
FIG. 5A-5C. Loss of SMARCAL1 in glioblastoma cell lines leads to features of ALT.
Figure 5:
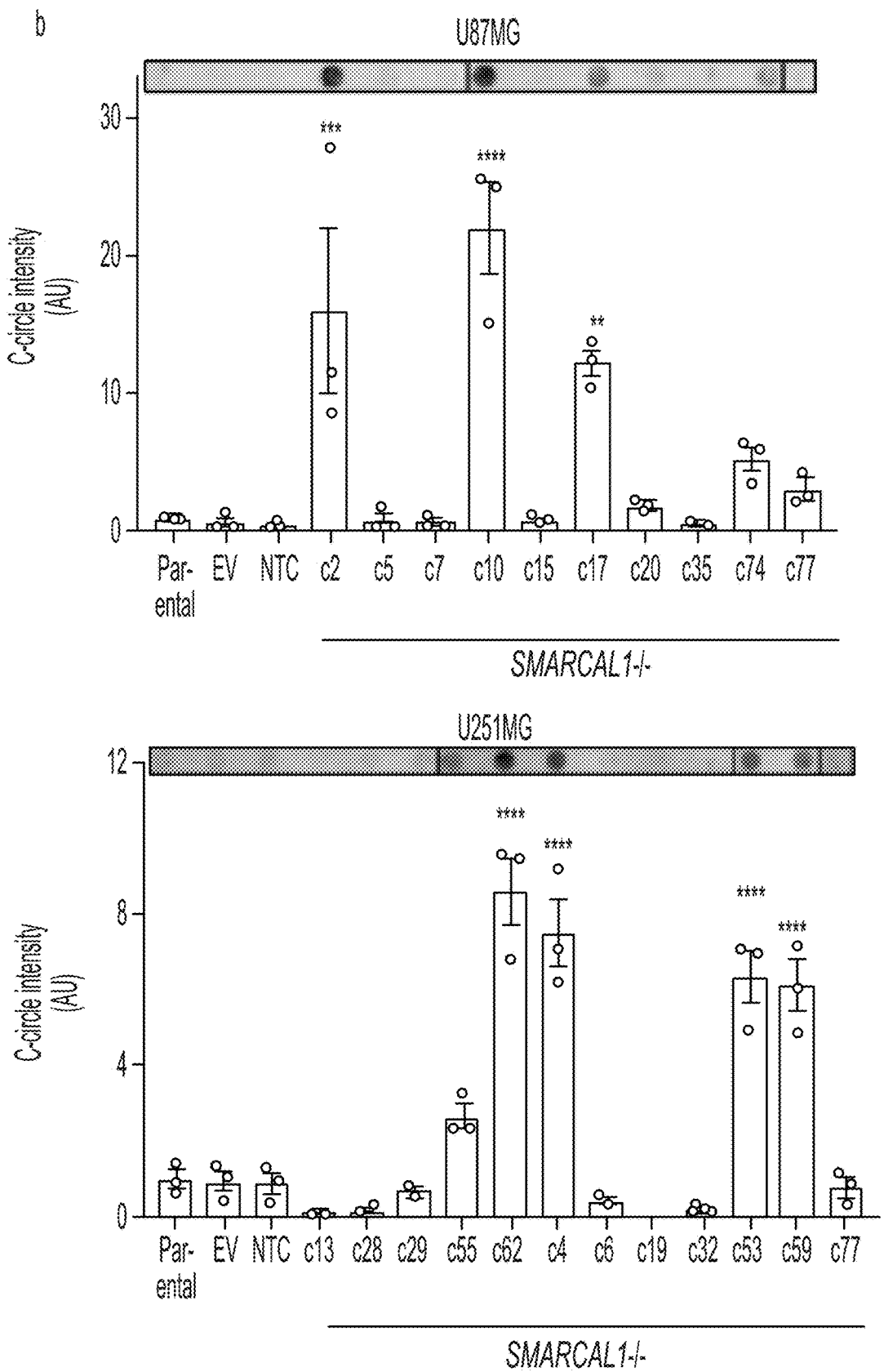
Figure 5:
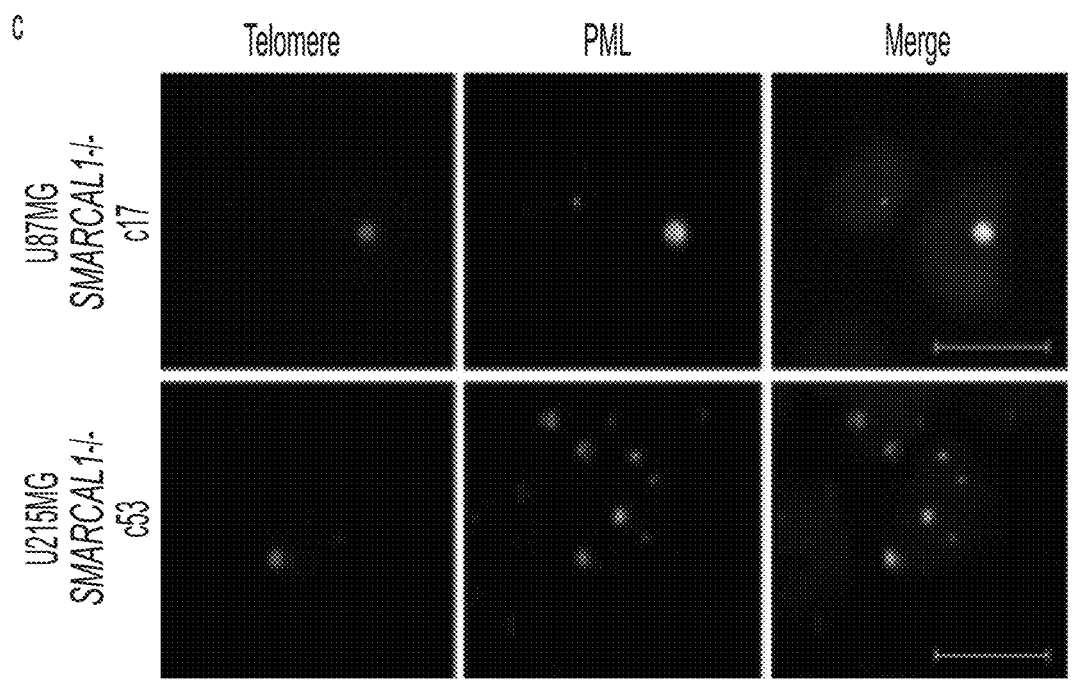

Finally, we investigated if knockout of SMARCAL1 is sufficient to induce hallmarks of ALT in GBM cell lines. We used CRISPR/Cas9 gene editing to generate SMARCAL1 knockout clones in the ALT-negative GBM cell lines U87MG and U251MG[36,37]. In total, 12 U251MG (A: 5 clones, B: 7 clones) and 10 U87MG (A: 2 clones, B: 9 clones) lines were validated as SMARCAL1 knockout clones using this approach (FIG. 5a, FIG. 12A-12B, Supplementary Data 11☐12 available on-line at Nature Communications as the supplementary data associated with the article at volume 9, page 2087). Isogenic SMARCAL1$^{-/-}$ GBM cell lines were assessed for accumulation of C-circles by dot blot. In both cell lines, 30% of isogenic SMARCAL1$^{-/-}$ clones isolated exhibited significantly increased levels of C-circles (FIG. 5B), as well as rare ultrabright telomere foci and APBs (FIG. 5C), indicating that loss of SMARCAL1 in GBM cells can induce signs of ALT.

REFERENCES

The disclosure of each reference cited is expressly incorporated herein.
1. Wen P Y, Kesari S. Malignant gliomas in adults. N. Engl. J. Med. 2008; 359:492☐507. doi: 10.1056/NEJMra0708126.
2. Ostrom Q T, et al. CBTRUS Statistical Report: primary brain and central nervous system tumors diagnosed in the United States in 2008-2012. Neuro. Oncol. 2015; 17:iv1☐iv62. doi: 10.1093/neuonc/nov189.
3. Henson J D, et al. A robust assay for alternative lengthening of telomeres in tumors shows the significance of alternative lengthening of telomeres in sarcomas and astrocytomas. Clin. Cancer Res. 2005; 11:217☐225.
4. Killela P J, et al. Mutations in IDH1, IDH2, and in the TERT promoter define clinically distinct subgroups of adult malignant gliomas. Oncotarget. 2014; 5:1515☐1525.
5. Killela P J, et al. TERT promoter mutations occur frequently in gliomas and a subset of tumors derived from cells with low rates of self-renewal. Proc. Natl. Acad. Sci. USA. 2013; 110:6021☐026. doi: 10.1073/pnas.1303607110.
6. Yan H, et al. IDH1 and IDH2 mutations in gliomas. N. Engl. J. Med. 2009; 360:765☐773. doi: 10.1056/NEJMoa0808710.
7. Parsons D W, et al. An integrated genomic analysis of human glioblastoma multiforme. Science. 2008; 321: 1807☐1812. doi: 10.1126/science.1164382.
8. Eckel-Passow J E, et al. Glioma groups based on 1p/19q, IDH, and TERT promoter mutations in tumors. N. Engl. J. Med. 2015; 372:2499☐2508. doi: 10.1056/NEJMoa1407279.
9. Louis, D. N. et al. WHO Classification of Tumours of the Central Nervous System. Revised 4th edition (International Agency for Research on Cancer, France, 2016).
10. Jiao Y, et al. Frequent ATRX, CIC, FUBP1 and IDH1 mutations refine the classification of malignant gliomas. Oncotarget. 2012; 3:709☐722. doi: 10.18632/oncotarget.588.
11. Zhang L, et al. Exome sequencing identifies somatic gain-of-function PPM1D mutations in brainstem gliomas. Nat. Genet. 2014; 46:726☐730. doi: 10.1038/ng.2995.

12. Killela P J, et al. The genetic landscape of anaplastic astrocytoma. Oncotarget. 2014; 5:1452□1457.
13. Heaphy C M, et al. Altered telomeres in tumors with ATRX and DAXX mutations. Science. 2011; 333:425. doi: 10.1126/science.1207313.
14. Huang F W, et al. Highly recurrent TERT promoter mutations in human melanoma. Science. 2013; 339: 957□959. doi: 10.1126/science.1229259.
15. Horn S, et al. TERT promoter mutations in familial and sporadic melanoma. Science. 2013; 339:959□961. doi: 10.1126/science.1230062.
16. Bell R J, et al. Cancer. The transcription factor GABP selectively binds and activates the mutant TERT promoter in cancer. Science. 2015; 348:1036□1039. doi: 10.1126/science.aab0015.
17. Heaphy C M, et al. Prevalence of the alternative lengthening of telomeres telomere maintenance mechanism in human cancer subtypes. Am. J. Pathol. 2011; 179: 1608□1615. doi: 10.1016/j.ajpath.2011.06.018.
18. de Wilde R F, et al. Loss of ATRX or DAXX expression and concomitant acquisition of the alternative lengthening of telomeres phenotype are late events in a small subset of MEN-1 syndrome pancreatic neuroendocrine tumors. Mod. Pathol. 2012; 25:1033□1039. doi: 10.1038/modpathol.2012.53.
19. Grobelny J V, Godwin A K, Broccoli D. ALT-associated PML bodies are present in viable cells and are enriched in cells in the G(2)/M phase of the cell cycle. J. Cell Sci. 2000; 113:4577□4585.
20. Henson J D, et al. DNA C-circles are specific and quantifiable markers of alternative-lengthening-of-telomeres activity. Nat. Biotechnol. 2009; 27:1181□1185. doi: 10.1038/nbt.1587.
21. Gonzalez-Perez A, et al. IntOGen-mutations identifies cancer drivers across tumor types. Nat. Methods. 2013; 10:1081□1082. doi: 10.1038/nmeth.2642.
22. Gonzalez-Perez A, Lopez-Bigas N. Functional impact bias reveals cancer drivers. Nucleic Acids Res. 2012; 40:e169. doi: 10.1093/nar/gks743.
23. Brennan C W, et al. The somatic genomic landscape of glioblastoma. Cell. 2013; 155:462□477. doi: 10.1016/j.cell.2013.09.034.
24. Couch F B, et al. ATR phosphorylates SMARCAL1 to prevent replication fork collapse. Genes Dev. 2013; 27:1610□1623. doi: 10.1101/gad.214080.113.
25. Bansbach C E, Betous R, Lovejoy C A, Glick G G, Cortez D. The annealing helicase SMARCAL1 maintains genome integrity at stalled replication forks. Genes Dev. 2009; 23:2405□2414. doi: 10.1101/gad.1839909.
26. Cox K E, Marechal A, Flynn R L. SMARCAL1 resolves replication stress at ALT telomeres. Cell Rep. 2016; 14:1032□1040. doi: 10.1016/j.celrep.2016.01.011.
27. Poole L A, et al. SMARCAL1 maintains telomere integrity during DNA replication. Proc. Natl. Acad. Sci. USA. 2015; 112:14864□14869. doi: 10.1073/pnas.1510750112.
28. Flaus A, Owen-Hughes T. Mechanisms for ATP-dependent chromatin remodelling: the means to the end. FEBS J. 2011; 278:3579□3595. doi: 10.1111/j.1742-4658.2011.08281.x.
29. Cesare A J, Griffith J D. Telomeric DNA in ALT cells is characterized by free telomeric circles and heterogeneous t-loops. Mol. Cell Biol. 2004; 24:9948□9957. doi: 10.1128/MCB.24.22.9948-9957.2004.
30. Rausch T, et al. DELLY: structural variant discovery by integrated paired-end and split-read analysis. Bioinformatics. 2012; 28:i333□i339. doi: 10.1093/bioinformatics/bts378.
31. Wu K J, et al. Direct activation of TERT transcription by c-MYC. Nat. Genet. 1999; 21:220□224. doi: 10.1038/6010.
32. Barretina J, et al. The Cancer Cell Line Encyclopedia enables predictive modelling of anticancer drug sensitivity. Nature. 2012; 483:603□607. doi: 10.1038/nature11003.
33. Yeager T R, et al. Telomerase-negative immortalized human cells contain a novel type of promyelocytic leukemia (PML) body. Cancer Res. 1999; 59:4175□4179.
34. Gao J, et al. Integrative analysis of complex cancer genomics and clinical profiles using the cBioPortal. Sci. Signal. 2013; 6:pl1. doi: 10.1126/scisignal.2004088.
35. Yusufzai T, Kadonaga J T. HARP is an ATP-driven annealing helicase. Science. 2008; 322:748□750. doi: 10.1126/science.1161233.
36. Patil V, Pal J, Somasundaram K. Elucidating the cancer-specific genetic alteration spectrum of glioblastoma derived cell lines from whole exome and RNA sequencing. Oncotarget. 2015; 6:43452□43471. doi: 10.18632/oncotarget.6171.
37. Ran F A, et al. Genome engineering using the CRISPR-Cas9 system. Nat. Protoc. 2013; 8:2281□2308. doi: 10.1038/nprot.2013.143.
38. Flynn R L, et al. Alternative lengthening of telomeres renders cancer cells hypersensitive to ATR inhibitors. Science. 2015; 347:273□277. doi: 10.1126/science.1257216.
39. Postow L, Woo E M, Chait B T, Funabiki H. Identification of SMARCAL1 as a component of the DNA damage response. J. Biol. Chem. 2009; 284: 35951□35961. doi: 10.1074/jbc.M109.048330.
40. Lugli N, Sotiriou S K, Halazonetis T D. The role of SMARCAL1 in replication fork stability and telomere maintenance. DNA Repair. 2017; 56:129□134. doi: 10.1016/j.dnarep.2017.06.015.
41. Boerkoel C F, et al. Mutant chromatin remodeling protein SMARCAL1 causes Schimke immuno-osseous dysplasia. Nat. Genet. 2002; 30:215□220. doi: 10.1038/ng821.
42. Baradaran-Heravi A, et al. SMARCAL1 deficiency predisposes to non-Hodgkin lymphoma and hypersensitivity to genotoxic agents in vivo. Am. J. Med. Genet. A. 2012; 158A:2204□2213. doi: 10.1002/ajmg.a.35532.
43. Carroll C, et al. Schimke immunoosseous dysplasia associated with undifferentiated carcinoma and a novel SMARCAL1 mutation in a child. Pediatr. Blood Cancer. 2013; 60:E88□E90. doi: 10.1002/pbc.24542.
44. Deguchi K, et al. Neurologic phenotype of Schimke immuno-osseous dysplasia and neurodevelopmental expression of SMARCAL1. J. Neuropathol. Exp. Neurol. 2008; 67:565□577. doi: 10.1097/NEN.0b013e3181772777.
45. Simon A J, et al. Novel SMARCAL1 bi-allelic mutations associated with a chromosomal breakage phenotype in a severe SIOD patient. J. Clin. Immunol. 2014; 34:76□83. doi: 10.1007/s10875-013-9957-3.
46. Cancer Genome Atlas Research Network et al. Comprehensive, integrative genomic analysis of diffuse lower-grade gliomas. N. Engl. J. Med. 2015; 372:2481□2498. doi: 10.1056/NEJMoa1402121.

47. Ceccarelli M, et al. Molecular profiling reveals biologically discrete subsets and pathways of progression in diffuse glioma. Cell. 2016; 164:550–563. doi: 10.1016/j.cell.2015.12.028.
48. Cancer Genome Atlas Research Network. Comprehensive and integrated genomic characterization of adult soft tissue sarcomas. Cell171, 950–965.e28 (2017).
49. Eastley N, et al. Telomere maintenance in soft tissue sarcomas. J. Clin. Pathol. 2017; 70:371–377. doi: 10.1136/jclinpath-2016-204151.
50. Matsuo T, et al. Telomeres and telomerase in sarcomas. Anticancer Res. 2009; 29:3833–3836.
51. Davis C F, et al. The somatic genomic landscape of chromophobe renal cell carcinoma. Cancer Cell. 2014; 26:319–330. doi: 10.1016/j.ccr.2014.07.014.
52. Valentijn L J, et al. TERT rearrangements are frequent in neuroblastoma and identify aggressive tumors. Nat. Genet. 2015; 47:1411–1414. doi: 10.1038/ng.3438.
53. Peifer M, et al. Telomerase activation by genomic rearrangements in high-risk neuroblastoma. Nature. 2015; 526:700–704. doi: 10.1038/nature14980.
54. Horbinski C. To BRAF or not to BRAF: is that even a question anymore? J. Neuropathol. Exp. Neurol. 2013; 72:2–7. doi: 10.1097/NEN.0b013e318279f3db.
55. Zhang J, et al. Combined BRAF(V600E) and MEK blockade for BRAF(V600E)-mutant gliomas. J. Neurooncol. 2017; 131:495–505. doi: 10.1007/s11060-016-2333-4.
56. Nicolaides T P, et al. Targeted therapy for BRAFV600E malignant astrocytoma. Clin. Cancer Res. 2011; 17:7595–7604. doi: 10.1158/1078-0432.CCR-11-1456.
57. Johanns T M, Ferguson C J, Grierson P M, Dahiya S, Ansstas G. Rapid clinical and radiographic response with combined dabrafenib and trametinib in adults with BRAF-mutated high-grade glioma. J. Natl. Compr. Canc. Netw. 2018; 16:4–10. doi: 10.6004/jnccn.2017.7032.
58. Jones S, et al. Personalized genomic analyses for cancer mutation discovery and interpretation. Sci. Transl. Med. 2015; 7:283ra253. doi: 10.1126/scitranslmed.aaa7161.
59. Li H, Durbin R. Fast and accurate short read alignment with Burrows-Wheeler transform. Bioinformatics. 2009; 25:1754–1760. doi: 10.1093/bioinformatics/btp324.
60. Cibulskis K, et al. Sensitive detection of somatic point mutations in impure and heterogeneous cancer samples. Nat. Biotechnol. 2013; 31:213–219. doi: 10.1038/nbt.2514.
61. Saunders C T, et al. Strelka: accurate somatic small-variant calling from sequenced tumor-normal sample pairs. Bioinformatics. 2012; 28:1811–1817. doi: 10.1093/bioinformatics/bts271.
62. Boeva V, et al. Control-FREEC: a tool for assessing copy number and allelic content using next-generation sequencing data. Bioinformatics. 2012; 28:423–425. doi: 10.1093/bioinformatics/btr670.
63. Wang K, Li M, Hakonarson H. ANNOVAR: functional annotation of genetic variants from high-throughput sequencing data. Nucleic Acids Res. 2010; 38:e164. doi: 10.1093/nar/gkq603.
64. Hsu P D, et al. DNA targeting specificity of RNA-guided Cas9 nucleases. Nat. Biotechnol. 2013; 31:827–832. doi: 10.1038/nbt.2647.
65. Doench J G, et al. Optimized sgRNA design to maximize activity and minimize off-target effects of CRISPR-Cas9. Nat. Biotechnol. 2016; 34:184–191. doi: 10.1038/nbt.3437.
66. Mavrakis K J, et al. Disordered methionine metabolism in MTAP/CDKN2A-deleted cancers leads to dependence on PRMT5. Science. 2016; 351:1208–1213. doi: 10.1126/science.aad5944.
67. Jiao Y, et al. DAXX/ATRX, MEN1, and mTOR pathway genes are frequently altered in pancreatic neuroendocrine tumors. Science. 2011; 331:1199–1203. doi: 10.1126/science.1200609.
68. Mangerel J, et al. Alternative lengthening of telomeres is enriched in, and impacts survival of TP53 mutant pediatric malignant brain tumors. Acta Neuropathol. 2014; 128:853–862. doi: 10.1007/s00401-014-1348-1.
69. Dimitrova N, Chen Y C, Spector D L, de Lange T. 53BP1 promotes non-homologous end joining of telomeres by increasing chromatin mobility. Nature. 2008; 456:524–528. doi: 10.1038/nature07433.
70. Hatanpaa K J, Burger P C, Eshleman J R, Murphy K M, Berg K D. Molecular diagnosis of oligodendroglioma in paraffin sections. Lab. Invest. 2003; 83:419–428. doi: 10.1097/01.LAB.0000059948.67795.EF.
71. Guzman C, Bagga M, Kaur A, Westermarck J, Abankwa D. ColonyArea: an ImageJ plugin to automatically quantify colony formation in clonogenic assays. PLoS One. 2014; 9:e92444. doi: 10.1371/journal.pone.0092444.

Clauses

1. A method for classifying a glioblastoma in a subject comprising: (1) obtaining a biological sample from the subject (2) determining at least one of the following: (a) the presence of one or more rearrangements and/or mutations in and/or upstream of the TERT gene, (b) rearrangements and/or mutations in the IDH gene, (c) rearrangement and/or mutations in the TERT promoter, (d) rearrangements and/or mutations in the SWI/SNF-related, matrix-associated, actin-dependent regulator of chromatin, subfamily A-like 1 (SMARCAL1); and (e) rearrangements and/or mutations in the ATRX gene, and (f) telomere activity; and (3) classifying the glioblastoma based on the genetic profile, where the presence of TERT rearrangements and telomere activation is indicative of $IDH^{WT}$-$TERT^{SV}$ glioblastoma, the present of SMARCAL1 and ATRX mutations with the exhibition of alternative lengthening of telomeres (ALT) is indicative of a $IDH^{WT}$-ALT glioblastoma, where ALT negative but lacking ALT-associated mutations or TERT rearrangements is indicative of a $IDH^{WT}$-other glioblastoma.

2. The method according to claim 1 further comprising the step of (4) administering an appropriate anti-glioblastoma therapy.

3. A method of diagnosing and/or prognosing a glioblastoma in a subject comprising, consisting of, or consisting essentially of: (1) obtaining a biological sample from the subject; (2) classifying the glioblastoma according to the method of claim 1; (3) determining the prognosis and/or diagnosis of the subject based on the classification; and (4) administering an appropriate anti-glioblastoma therapy.

4. The method as in any of the preceding claims in which the biological sample is selected from the group consisting of tissues, cells, biopsies, blood, lymph, serum, plasma, urine, saliva, mucus, and tears.

5. The method according to claim 4 in which the sample comprises a serum sample or blood sample.

6. A kit for classifying a glioblastoma in a subject comprising means for classifying a glioblastoma from a biological sample as provided herein and instructions for use.

7. All that is described and illustrated herein.

We claim:

1. A method of treating a glioma tumor of a human comprising:

selecting a glioma tumor of a human, said tumor comprising wild-type IDH1, wild-type IDH2, and wild-type promoter of TERT gene;

testing for and identifying a somatic structural rearrangement in the chromosome region upstream from TERT gene in the glioma tumor of the human using a structural rearrangement assay; and treating the human with a telomerase targeted therapy.

2. The method of claim 1 wherein the structural rearrangement is selected from the group consisting of an inversion, a duplication, and a translocation.

3. The method of claim 1 wherein the structural rearrangement assay is a break-apart Flourescence In-situ Hybridization (FISH) assay.

4. The method of claim 1 wherein the structural rearrangement assay utilizes a first probe that hybridizes upstream of TERT gene and a second probe that hybridizes within or downstream of the TERT gene.

5. The method of claim 1 wherein the structural rearrangement assay utilizes junction-spanning PCR.

6. The method of claim 1 wherein the telomerase targeted therapy is a human TERT (hTERT) derived peptide vaccine.

7. The method of claim 1 wherein the telomerase targeted therapy is an antisense oligonucleotide.

8. The method of claim 1 wherein the telomerase targeted therapy is a small molecule inhibitor of TERT.

9. The method of claim 1 wherein the glioma tumor is further selected for having no mutant IDH1, no mutant IDH2, and no mutant TERT promoter.

10. A method of treating a glioma tumor of a human comprising:

testing the glioma tumor of the human, to determine its genotype (a) at codon 132 of isocitrate dehydrogenase 1 (IDH1) gene, (b) at codon 172 of isocitrate dehydrogenase 2 (IDH2) gene, and (c) at nucleotides -124 and -146 of promoter of telomerase reverse transcriptase (TERT) gene, and to determine (d) its structural arrangement on a region of chromosome 5 upstream from TERT gene; and treating the human with a telomerase targeted therapy.

11. The method of claim 10 wherein the human is treated when the glioma tumor is found to have a wild-type codon 132 of IDH1 gene, a wild-type codon 172 of IDH2 gene, a wild-type TERT promoter at nucleotides -124 and -146, and a structural rearrangement of the region of chromosome 5 upstream from TERT gene.

12. The method of claim 11 wherein the structural rearrangement is selected from the group consisting of an inversion, a duplication, and a translocation.

13. The method of claim 10 wherein the structural arrangement is assayed using a break-apart Flourescence In-situ Hybridization (FISH) assay.

14. The method of claim 10 wherein the structural arrangement is assayed utilizing a first probe that hybridizes upstream of TERT gene and a second probe that hybridizes within or downstream of the TERT gene.

15. The method of claim 10 wherein the structural arrangement is assayed utilizing junction-spanning PCR.

16. The method of claim 10 wherein the telomerase targeted therapy is a human TERT (hTERT) derived peptide vaccine.

17. The method of claim 10 wherein the telomerase targeted therapy is an antisense oligonucleotide.

18. The method of claim 10 wherein the telomerase targeted therapy is a small molecule inhibitor of TERT.

* * * * *